(12) United States Patent
Johnson et al.

(10) Patent No.: US 7,276,068 B2
(45) Date of Patent: *Oct. 2, 2007

(54) VESSEL SEALING INSTRUMENT WITH ELECTRICAL CUTTING MECHANISM

(75) Inventors: Kristin Johnson, Louisville, CO (US); Gary M. Couture, Boulder, CO (US); Jeff Unger, Boulder, CO (US); Robert Sharp, Boulder, CO (US)

(73) Assignee: Sherwood Services AG, Schaffhausen (CH)

( * ) Notice: Subject to any disclaimer, the term of this patent is extended or adjusted under 35 U.S.C. 154(b) by 455 days.

This patent is subject to a terminal disclaimer.

(21) Appl. No.: 10/932,612

(22) Filed: Sep. 2, 2004

(65) Prior Publication Data

US 2005/0113826 A1  May 26, 2005

Related U.S. Application Data

(63) Continuation-in-part of application No. PCT/US03/28539, filed on Sep. 11, 2003.

(60) Provisional application No. 60/416,064, filed on Oct. 4, 2002.

(51) Int. Cl.
  *A61B 18/18* (2006.01)
(52) U.S. Cl. .......................... 606/51; 606/45
(58) Field of Classification Search ................ 606/41, 606/45–52
See application file for complete search history.

(56) References Cited

U.S. PATENT DOCUMENTS 371,664 A  10/1887  Brannan et al.

| | | |
|---|---|---|
| 702,472 A | 6/1902 | Pignolet |
| 728,883 A | 5/1903 | Downes |
| 1,586,645 A | 6/1926 | Bierman |

(Continued)

FOREIGN PATENT DOCUMENTS

CA  2104423  2/1994

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner*—Michael Peffley

(57) ABSTRACT

An end effector assembly for use with an instrument for sealing vessels and cutting vessels includes a pair of opposing first and second jaw members which are movable relative to one another from a first spaced apart position to a second position for grasping tissue therebetween. Each jaw member includes a pair of spaced apart electrically conductive tissue contacting surfaces which each have an insulator disposed therebetween, the conductive surfaces are connected to an electrosurgical energy source. The first jaw member includes an electrically conductive cutting element disposed within the insulator which extends towards the second tissue contacting surface to create a gap therebetween. The cutting element is inactive during the sealing process while the two pairs of electrically conductive surfaces are activated to seal tissue. During the cutting process, the cutting element is energized to a first potential and at least one electrically conductive tissue contacting surface is energized to a different potential to effect a tissue cut through the tissue held between the jaw members along the already formed tissue seal.

13 Claims, 9 Drawing Sheets

U.S. PATENT DOCUMENTS

| | | |
|---|---|---|
| 2,002,594 A | 5/1935 | Wappler et al. |
| 2,011,169 A | 8/1935 | Wappler |
| 2,031,682 A | 2/1936 | Wappler et al. |
| 2,176,479 A | 10/1939 | Willis |
| 2,305,156 A | 4/1941 | Grubel |
| 2,632,661 A | 8/1948 | Cristofv |
| 2,668,538 A | 2/1954 | Baker |
| 2,796,065 A | 6/1957 | Kapp |
| 3,459,187 A | 3/1967 | Pallotta |
| 3,643,663 A | 2/1972 | Sutter |
| 3,651,811 A | 3/1972 | Hildebrandt et al. |
| 3,862,630 A | 1/1975 | Balamuth |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,300,564 A | 11/1981 | Furihata |
| 4,370,980 A | 2/1983 | Lottick |
| 4,416,276 A | 11/1983 | Newton et al. |
| 4,452,246 A | 6/1984 | Bader et al. |
| 4,492,231 A | 1/1985 | Auth |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Koch et al. |
| D295,893 S | 5/1988 | Sharkany et al. |
| D295,894 S | 5/1988 | Sharkany et al. |
| 4,763,669 A | 8/1988 | Jaeger |
| 4,827,929 A | 5/1989 | Hodge |
| 4,887,612 A | 12/1989 | Esser et al. |
| 4,938,761 A | 7/1990 | Ensslin |
| 4,985,030 A | 1/1991 | Melzer et al. |
| 5,007,908 A | 4/1991 | Rydell |
| 5,026,370 A | 6/1991 | Lottick |
| 5,084,057 A | 1/1992 | Green et al. |
| 5,099,840 A | 3/1992 | Goble et al. |
| 5,116,332 A | 5/1992 | Lottick |
| 5,147,357 A | 9/1992 | Rose et al. |
| 5,151,102 A | 9/1992 | Kamiyama et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,290,286 A | 3/1994 | Parins |
| 5,304,203 A | 4/1994 | El-Mallawany et al. |
| 5,308,357 A | 5/1994 | Lichtman |
| 5,318,589 A | 6/1994 | Lichtman |
| 5,324,289 A | 6/1994 | Eggers |
| 5,330,471 A | 7/1994 | Eggers |
| 5,334,183 A | 8/1994 | Wuchinich |
| 5,334,215 A | 8/1994 | Chen |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,383,897 A | 1/1995 | Wholey |
| 5,389,098 A | 2/1995 | Tsuruta et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,411,519 A | 5/1995 | Tovey et al. |
| 5,411,520 A | 5/1995 | Nash et al. |
| 5,413,571 A | 5/1995 | Katsaros et al. |
| 5,415,657 A | 5/1995 | Taymor-Luria |
| 5,422,567 A | 6/1995 | Matsunaga |
| 5,423,810 A | 6/1995 | Goble et al. |
| 5,425,739 A | 6/1995 | Jessen |
| 5,429,616 A | 7/1995 | Schaffer |
| 5,431,674 A | 7/1995 | Basile et al. |
| 5,437,292 A | 8/1995 | Kipshidze et al. |
| 5,438,302 A | 8/1995 | Goble |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,451,224 A | 9/1995 | Goble et al. |
| 5,456,684 A | 10/1995 | Schmidt et al. |
| 5,458,598 A | 10/1995 | Feinberg et al. |
| 5,460,629 A | 10/1995 | Shlain et al. |
| 5,462,546 A | 10/1995 | Rydell |
| 5,472,443 A | 12/1995 | Cordis et al. |
| 5,478,351 A | 12/1995 | Meade et al. |
| 5,480,409 A | 1/1996 | Riza |
| 5,484,436 A | 1/1996 | Eggers et al. |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,715 A | 7/1996 | Katsaros et al. |
| 5,542,945 A | 8/1996 | Fritzsch |
| 5,558,672 A | 9/1996 | Edwards et al. |
| 5,562,699 A | 10/1996 | Heimberger et al. |
| 5,569,241 A | 10/1996 | Edwards |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,578,052 A | 11/1996 | Koros et al. |

| | | | | | | |
|---|---|---|---|---|---|---|
| 5,582,611 A | 12/1996 | Tsuruta et al. | | 5,921,984 A | 7/1999 | Sutcu et al. |
| 5,585,896 A | 12/1996 | Yamazaki et al. | | 5,925,043 A | 7/1999 | Kumar et al. |
| 5,590,570 A | 1/1997 | LeMaire, III et al. | | 5,935,126 A | 8/1999 | Riza |
| 5,601,601 A | 2/1997 | Tal et al. | | 5,944,718 A | 8/1999 | Austin et al. |
| 5,603,711 A | 2/1997 | Parins et al. | | 5,951,549 A | 9/1999 | Richardson et al. |
| 5,603,723 A | 2/1997 | Aranyi et al. | | 5,954,720 A | 9/1999 | Wilson et al. |
| 5,611,798 A | 3/1997 | Eggers | | 5,957,923 A | 9/1999 | Hahnen et al. |
| 5,626,578 A | 5/1997 | Tihon | | 5,961,514 A | 10/1999 | Long et al. |
| 5,626,609 A | 5/1997 | Zvenyatsky et al. | | 5,976,132 A | 11/1999 | Morris |
| 5,630,833 A | 5/1997 | Katsaros et al. | | 5,984,939 A | 11/1999 | Yoon |
| 5,637,110 A | 6/1997 | Pennybacker et al. | | 5,989,277 A | 11/1999 | LeMaire, III et al. |
| 5,643,294 A | 7/1997 | Tovey et al. | | 6,004,335 A | 12/1999 | Vaitekunas et al. |
| 5,647,869 A | 7/1997 | Goble et al. | | 6,010,516 A | 1/2000 | Hulka |
| 5,647,871 A | 7/1997 | Levine et al. | | 6,024,741 A | 2/2000 | Williamson et al. |
| 5,649,959 A | 7/1997 | Hannam et al. | | 6,024,744 A | 2/2000 | Kese et al. |
| 5,658,281 A | 8/1997 | Heard | | 6,030,384 A | 2/2000 | Nezhat |
| 5,662,667 A | 9/1997 | Knodel | | 6,033,399 A | 3/2000 | Gines |
| 5,665,100 A | 9/1997 | Yoon | | 6,039,733 A | 3/2000 | Buysse et al. |
| 5,667,526 A | 9/1997 | Levin | | 6,041,679 A | 3/2000 | Slater et al. |
| 5,674,220 A | 10/1997 | Fox et al. | | 6,050,996 A | 4/2000 | Schmaltz et al. |
| 5,681,282 A | 10/1997 | Eggers et al. | | 6,053,914 A | 4/2000 | Eggers et al. |
| 5,693,051 A | 12/1997 | Schulze et al. | | 6,053,933 A | 4/2000 | Balazs et al. |
| 5,695,522 A | 12/1997 | LeMaire, III et al. | | D424,694 S | 5/2000 | Tetzlaff et al. |
| 5,700,261 A | 12/1997 | Brinkerhoff | | D425,201 S | 5/2000 | Tetzlaff et al. |
| 5,702,390 A | 12/1997 | Austin et al. | | 6,059,782 A | 5/2000 | Novak et al. |
| 5,707,369 A | 1/1998 | Vaitekunas et al. | | RE36,795 E | 7/2000 | Rydell |
| 5,709,680 A | 1/1998 | Yates et al. | | 6,083,223 A | 7/2000 | Baker |
| 5,716,366 A | 2/1998 | Yates | | 6,086,586 A | 7/2000 | Hooven |
| 5,720,744 A | 2/1998 | Eggleston et al. | | 6,090,107 A | 7/2000 | Borgmeier et al. |
| 5,727,428 A | 3/1998 | LeMaire, III et al. | | 6,096,037 A | 8/2000 | Mulier et al. |
| 5,735,848 A | 4/1998 | Yates et al. | | 6,099,550 A | 8/2000 | Yoon |
| 5,743,906 A | 4/1998 | Parins et al. | | 6,102,909 A | 8/2000 | Chen et al. |
| 5,755,717 A | 5/1998 | Yates et al. | | 6,110,171 A | 8/2000 | Rydell |
| 5,766,130 A | 6/1998 | Selmonosky | | 6,113,596 A | 9/2000 | Hooven et al. |
| 5,766,166 A | 6/1998 | Hooven | | 6,113,598 A | 9/2000 | Baker |
| 5,766,170 A | 6/1998 | Eggers | | 6,117,158 A | 9/2000 | Measamer et al. |
| 5,769,849 A | 6/1998 | Eggers | | 6,123,701 A | 9/2000 | Nezhat |
| 5,772,655 A | 6/1998 | Bauer et al. | | H1904 H | 10/2000 | Yates et al. |
| 5,772,670 A | 6/1998 | Brosa | | 6,126,658 A | 10/2000 | Baker |
| 5,776,128 A | 7/1998 | Eggers | | 6,152,923 A | 11/2000 | Ryan |
| 5,776,130 A | 7/1998 | Buysse et al. | | 6,162,220 A | 12/2000 | Nezhat |
| 5,779,701 A | 7/1998 | McBrayer et al. | | 6,174,309 B1 | 1/2001 | Wrublewski et al. |
| 5,792,137 A | 8/1998 | Carr et al. | | 6,179,834 B1 | 1/2001 | Buysse et al. |
| 5,792,177 A | 8/1998 | Kaseda | | 6,179,837 B1 | 1/2001 | Hooven |
| 5,797,938 A | 8/1998 | Paraschac et al. | | 6,183,467 B1 | 2/2001 | Shapeton et al. |
| 5,797,958 A | 8/1998 | Yoon | | 6,187,003 B1 | 2/2001 | Buysse et al. |
| 5,800,449 A | 9/1998 | Wales | | 6,190,386 B1 | 2/2001 | Rydell |
| 5,807,393 A | 9/1998 | Williamson, IV et al. | | 6,193,718 B1 | 2/2001 | Kortenbach et al. |
| 5,810,808 A | 9/1998 | Eggers | | 6,206,876 B1 | 3/2001 | Levine et al. |
| 5,810,811 A * | 9/1998 | Yates et al. .................. 606/50 | | 6,206,877 B1 | 3/2001 | Kese et al. |
| 5,810,877 A | 9/1998 | Roth et al. | | 6,217,602 B1 | 4/2001 | Redmon |
| 5,814,043 A | 9/1998 | Shapeton | | 6,221,039 B1 | 4/2001 | Durgin et al. |
| 5,817,083 A | 10/1998 | Williamson, IV et al. | | 6,224,593 B1 | 5/2001 | Ryan et al. |
| 5,820,630 A | 10/1998 | Lind | | 6,228,080 B1 | 5/2001 | Gines |
| 5,827,271 A | 10/1998 | Buysse et al. | | 6,228,083 B1 | 5/2001 | Lands et al. |
| 5,827,279 A | 10/1998 | Hughett et al. | | 6,267,761 B1 | 7/2001 | Ryan |
| 5,827,281 A | 10/1998 | Levin | | 6,270,497 B1 | 8/2001 | Sekino et al. |
| 5,833,690 A | 11/1998 | Yates et al. | | 6,270,508 B1 | 8/2001 | Klieman et al. |
| 5,843,080 A | 12/1998 | Fleenor et al. | | 6,273,887 B1 | 8/2001 | Yamauchi et al. |
| 5,849,022 A | 12/1998 | Sakashita et al. | | 6,277,117 B1 | 8/2001 | Tetzlaff et al. |
| 5,853,412 A | 12/1998 | Mayenberger | | 6,280,458 B1 | 8/2001 | Boche et al. |
| 5,860,976 A | 1/1999 | Billings et al. | | 6,283,961 B1 | 9/2001 | Underwood et al. |
| 5,876,401 A | 3/1999 | Schulze et al. | | D449,886 S | 10/2001 | Tetzlaff et al. |
| 5,891,141 A | 4/1999 | Rydell | | 6,322,561 B1 | 11/2001 | Eggers et al. |
| 5,891,142 A | 4/1999 | Eggers et al. | | 6,334,860 B1 | 1/2002 | Dorn |
| 5,893,863 A | 4/1999 | Yoon | | 6,334,861 B1 | 1/2002 | Chandler et al. |
| 5,893,875 A | 4/1999 | O'Connor et al. | | 6,345,532 B1 | 2/2002 | Coudray et al. |
| 5,893,877 A | 4/1999 | Gampp, Jr. et al. | | 6,350,264 B1 | 2/2002 | Hooven |
| 5,902,301 A | 5/1999 | Olig | | 6,352,536 B1 | 3/2002 | Buysse et al. |
| 5,906,630 A | 5/1999 | Anderhub et al. | | D457,958 S | 5/2002 | Dycus et al. |
| 5,908,420 A | 6/1999 | Parins et al. | | D457,959 S | 5/2002 | Tetzlaff et al. |
| 5,911,719 A | 6/1999 | Eggers | | 6,387,094 B1 | 5/2002 | Eitenmuller |
| 5,913,874 A | 6/1999 | Berns et al. | | 6,398,779 B1 | 6/2002 | Buysse et al. |

| | | | | | | |
|---|---|---|---|---|---|---|
| 6,402,747 B1 | 6/2002 | Lindemann et al. | | 7,160,298 B2 | 1/2007 | Lawes et al. |
| 6,409,728 B1 | 6/2002 | Ehr et al. | | 7,160,299 B2 | 1/2007 | Baily |
| H2037 H | 7/2002 | Yates et al. | | 7,179,258 B2 | 2/2007 | Buysse et al. |
| 6,419,675 B1 | 7/2002 | Gallo, Sr. | | 7,195,631 B2 | 3/2007 | Dumbauld |
| 6,425,896 B1 | 7/2002 | Baltschun et al. | | 2002/0013583 A1 | 1/2002 | Camram et al. |
| 6,440,144 B1 | 8/2002 | Bacher | | 2002/0049442 A1 | 4/2002 | Roberts et al. |
| 6,443,952 B1 | 9/2002 | Mulier et al. | | 2002/0099372 A1 | 7/2002 | Schulze et al. |
| 6,443,970 B1 | 9/2002 | Schulze et al. | | 2002/0107517 A1 | 8/2002 | Witt et al. |
| 6,451,018 B1 | 9/2002 | Lands et al. | | 2002/0111624 A1 | 8/2002 | Witt et al. |
| 6,458,128 B1 | 10/2002 | Schulze | | 2002/0188294 A1 | 12/2002 | Couture et al. |
| 6,458,130 B1 | 10/2002 | Frazier et al. | | 2003/0014052 A1 | 1/2003 | Buysse et al. |
| 6,464,701 B1 | 10/2002 | Hooven et al. | | 2003/0014053 A1 | 1/2003 | Nguyen et al. |
| 6,464,702 B2 | 10/2002 | Schulze et al. | | 2003/0018331 A1 | 1/2003 | Dycus et al. |
| 6,464,704 B2 | 10/2002 | Schmaltz et al. | | 2003/0018332 A1 | 1/2003 | Schmaltz et al. |
| 6,511,480 B1 | 1/2003 | Tetzlaff et al. | | 2003/0032956 A1 | 2/2003 | Lands et al. |
| 6,527,771 B1 | 3/2003 | Weadock et al. | | 2003/0069571 A1 | 4/2003 | Treat et al. |
| 6,773,434 B2 | 3/2003 | Ciarrocca | | 2003/0078578 A1 | 4/2003 | Csaba et al. |
| 6,585,735 B1 | 7/2003 | Lands et al. | | 2003/0109875 A1 | 6/2003 | Tetzlaff et al. |
| 6,620,161 B2 | 9/2003 | Schulze et al. | | 2003/0114851 A1 | 6/2003 | Truckai et al. |
| 6,626,901 B1 | 9/2003 | Treat et al. | | 2003/0139741 A1 | 7/2003 | Goble et al. |
| 6,641,595 B1 | 11/2003 | Moran et al. | | 2003/0139742 A1 | 7/2003 | Wampler et al. |
| 6,652,521 B2 | 11/2003 | Schulze | | 2003/0158549 A1 | 8/2003 | Swanson |
| 6,656,177 B2 | 12/2003 | Truckai et al. | | 2003/0181910 A1 | 9/2003 | Dycus et al. |
| 6,669,696 B2 | 12/2003 | Bacher et al. | | 2003/0199869 A1 | 10/2003 | Johnson et al. |
| 6,682,528 B2 | 1/2004 | Frazier et al. | | 2003/0216732 A1 | 11/2003 | Truckai et al. |
| 6,685,724 B1 | 2/2004 | Haluck | | 2003/0220637 A1 | 11/2003 | Truckai et al. |
| 6,695,840 B2 | 2/2004 | Schulze | | 2003/0229344 A1 | 12/2003 | Dycus et al. |
| 6,726,068 B2 | 4/2004 | Miller | | 2004/0030330 A1 | 2/2004 | Brassell et al. |
| 6,726,686 B2 | 4/2004 | Buysse et al. | | 2004/0030332 A1 | 2/2004 | Knowlton et al. |
| 6,733,498 B2 | 5/2004 | Paton et al. | | 2004/0049185 A1 | 3/2004 | Latterell et al. |
| 6,736,813 B2 * | 5/2004 | Yamauchi et al. ............ 606/48 | | 2003/0082952 A1 | 4/2004 | Dycus et al. |
| 6,743,229 B2 | 6/2004 | Buysse et al. | | 2004/0064151 A1 | 4/2004 | Mollenauer |
| 6,770,072 B1 | 8/2004 | Truckai et al. | | 2004/0087943 A1 | 5/2004 | Dycus et al. |
| 6,776,780 B2 | 8/2004 | Mulier et al. | | 2004/0115296 A1 | 6/2004 | Duffin |
| 6,790,217 B2 | 9/2004 | Schulze et al. | | 2004/0116924 A1 | 6/2004 | Dycus et al. |
| D496,997 S | 10/2004 | Dycus et al. | | 2004/0116979 A1 | 6/2004 | Truckai et al. |
| 6,802,843 B2 | 10/2004 | Truckai et al. | | 2004/0122423 A1 | 6/2004 | Dycus et al. |
| D499,181 S | 11/2004 | Dycus et al. | | 2004/0143263 A1 | 7/2004 | Schechter et al. |
| 6,816,000 B2 | 11/2004 | Muller et al. | | 2004/0147925 A1 | 7/2004 | Buysse et al. |
| 6,818,000 B2 | 11/2004 | Muller et al. | | 2004/0162557 A1 | 8/2004 | Tetzlaff et al. |
| 6,821,273 B2 * | 11/2004 | Mollenauer .................. 606/28 | | 2004/0176762 A1 | 9/2004 | Lawes et al. |
| 6,887,240 B1 | 5/2005 | Lands et al. | | 2003/0236325 A1 | 11/2004 | Tetzlaff et al. |
| 6,926,716 B2 | 8/2005 | Baker et al. | | 2004/0225288 A1 | 11/2004 | Buysse et al. |
| 6,929,644 B2 | 8/2005 | Truckai et al. | | 2004/0230189 A1 | 11/2004 | Keppel |
| 6,932,810 B2 | 8/2005 | Ryan | | 2004/0243125 A1 | 12/2004 | Dycus et al. |
| 6,932,816 B2 | 8/2005 | Phan | | 2004/0249371 A1 | 12/2004 | Dycus et al. |
| 6,942,662 B2 | 9/2005 | Goble et al. | | 2004/0249374 A1 | 12/2004 | Tetzlaff et al. |
| 6,960,210 B2 | 11/2005 | Lands et al. | | 2004/0250419 A1 | 12/2004 | Sremcich et al. |
| 6,964,662 B2 | 11/2005 | Kidooka | | 2004/0254573 A1 | 12/2004 | Dycus et al. |
| 6,994,707 B2 | 2/2006 | Ellman et al. | | 2005/0004564 A1 | 1/2005 | Wham et al. |
| 7,011,657 B2 | 3/2006 | Truckai et al. | | 2005/0004568 A1 | 1/2005 | Lawes et al. |
| 7,033,354 B2 | 4/2006 | Keppel | | 2005/0004570 A1 | 1/2005 | Chapman et al. |
| 7,052,496 B2 | 5/2006 | Yamauchi | | 2005/0021025 A1 | 1/2005 | Buysse et al. |
| D525,361 S | 7/2006 | Hushka | | 2005/0021026 A1 | 1/2005 | Baily |
| 7,083,618 B2 | 8/2006 | Couture et al. | | 2005/0021027 A1 | 1/2005 | Shields et al. |
| 7,090,673 B2 | 8/2006 | Dycus et al. | | 2005/0033278 A1 | 2/2005 | McClurken et al. |
| 7,101,371 B2 | 9/2006 | Dycus et al. | | 2005/0101951 A1 | 5/2005 | Wham et al. |
| 7,101,372 B2 | 9/2006 | Dycus et al. | | 2005/0101952 A1 | 5/2005 | Lands et al. |
| 7,101,373 B2 | 9/2006 | Dycus et al. | | 2005/0107784 A1 | 5/2005 | Moses et al. |
| 7,103,947 B2 | 9/2006 | Sartor et al. | | 2005/0107785 A1 | 5/2005 | Dycus et al. |
| 7,112,199 B2 | 9/2006 | Cosmescu | | 2005/0113818 A1 | 5/2005 | Sartor et al. |
| D531,311 S | 10/2006 | Guerra et al. | | 2005/0113819 A1 | 5/2005 | Wham et al. |
| 7,118,570 B2 | 10/2006 | Tetzlaff et al. | | 2005/0113826 A1 | 5/2005 | Johnson et al. |
| 7,118,587 B2 | 10/2006 | Dycus et al. | | 2005/0113827 A1 | 5/2005 | Dumbauld et al. |
| 7,131,970 B2 | 11/2006 | Moses et al. | | 2005/0113828 A1 | 5/2005 | Shields et al. |
| 7,131,971 B2 | 11/2006 | Dycus et al. | | 2005/0119655 A1 | 6/2005 | Moses et al. |
| 7,135,020 B2 | 11/2006 | Lawes et al. | | 2005/0149151 A1 | 7/2005 | Orszulak et al. |
| D533,942 S | 12/2006 | Kerr et al. | | 2006/0064085 A1 | 3/2006 | Schechter et al. |
| 7,147,638 B2 | 12/2006 | Chapman et al. | | 2006/0079891 A1 | 4/2006 | Arts et al. |
| 7,150,097 B2 | 12/2006 | Sremcich et al. | | 2006/0129146 A1 | 6/2006 | Dycus et al. |
| 7,150,749 B2 | 12/2006 | Dycus et al. | | 2006/0161150 A1 | 7/2006 | Keppel |
| D535,027 S | 1/2007 | James et al. | | 2006/0167450 A1 | 7/2006 | Johnson et al. |
| 7,156,846 B2 | 1/2007 | Dycus et al. | | 2006/0167452 A1 | 7/2006 | Moses et al. |

| | | | |
|---|---|---|---|
| 2006/0173452 A1 | 8/2006 | Buysse et al. | |
| 2006/0189980 A1 | 8/2006 | Johnson et al. | |
| 2006/0189981 A1 | 8/2006 | Dycus et al. | |
| 2006/0190035 A1 | 8/2006 | Hushka et al. | |
| 2006/0217709 A1 | 9/2006 | Couture et al. | |
| 2006/0224158 A1 | 10/2006 | Odom et al. | |
| 2006/0259036 A1 | 11/2006 | Tetzlaf et al. | |
| 2006/0264922 A1 | 11/2006 | Sartor et al. | |
| 2006/0264931 A1 | 11/2006 | Chapman et al. | |
| 2006/0271038 A1 | 11/2006 | Johnson et al. | |
| 2007/0043352 A1 | 2/2007 | Garrison et al. | |
| 2007/0043353 A1 | 2/2007 | Dycus et al. | |
| 2007/0055231 A1 | 3/2007 | Dycus et al. | |
| 2007/0062017 A1 | 3/2007 | Dycus et al. | |

FOREIGN PATENT DOCUMENTS

| | | |
|---|---|---|
| DE | 2415263 | 10/1975 |
| DE | 2627679 | 1/1977 |
| DE | 8712328 | 3/1988 |
| DE | 4303882 | 8/1994 |
| DE | 29616210 | 1/1997 |
| DE | 19608716 | 4/1997 |
| DE | 19751106 | 5/1998 |
| DE | 19751108 | 5/1999 |
| EP | 0364216 A1 | 4/1990 |
| EP | 518230 A1 | 12/1992 |
| EP | 0 541 930 B1 | 5/1993 |
| EP | 0572131 | 12/1993 |
| EP | 584787 A1 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159928 A2 | 12/2001 |
| EP | 1301135 A | 4/2003 |
| EP | 1330991 A1 | 7/2003 |
| EP | 1486177 A2 | 6/2004 |
| EP | 1532932 A1 | 5/2005 |
| EP | 1645238 A1 | 4/2006 |
| EP | 1707143 A1 | 10/2006 |
| GB | 2214430 A | 6/1989 |
| JP | 501068 | 9/1984 |
| JP | 502328 | 3/1992 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 11/1974 |
| WO | WO89/00757 | 1/1989 |
| WO | WO92/06642 | 4/1992 |
| WO | WO94/08524 A | 4/1994 |
| WO | WO 94/08524 A | 4/1994 |
| WO | WO94/20025 | 9/1994 |
| WO | WO95/02369 | 1/1995 |
| WO | WO95/07662 | 3/1995 |
| WO | WO95/15124 | 6/1995 |
| WO | WO96/05776 | 2/1996 |
| WO | WO96/022056 | 7/1996 |
| WO | WO 96/13218 | 9/1996 |
| WO | WO96/13218 | 9/1996 |
| WO | WO97/00646 | 1/1997 |
| WO | WO97/00647 | 1/1997 |
| WO | WO97/10764 | 3/1997 |
| WO | WO97/24073 | 7/1997 |
| WO | WO97/24993 | 7/1997 |
| WO | WO98/27880 | 7/1998 |
| WO | WO99/03407 | 1/1999 |
| WO | WO99/03408 | 1/1999 |
| WO | WO99/03409 | 1/1999 |
| WO | WO99/12488 A | 3/1999 |
| WO | WO 99/12488 A | 3/1999 |
| WO | WO99/40857 | 8/1999 |
| WO | WO99/040861 | 8/1999 |
| WO | WO99/51158 | 10/1999 |
| WO | WO99/066850 | 12/1999 |
| WO | WO 99/66850 A | 12/1999 |
| WO | WO 99/66850 A | 12/1999 |
| WO | WO 00/24330 | 5/2000 |
| WO | WO 00/24331 | 5/2000 |
| WO | WO00/24331 | 5/2000 |
| WO | WO 00/41638 | 7/2000 |
| WO | WO00/47124 | 8/2000 |
| WO | WO 00/53112 | 9/2000 |
| WO | WO 01/17448 A | 3/2001 |
| WO | WO 01/54604 | 8/2001 |
| WO | WO02/07627 | 1/2002 |
| WO | WO 02/07627 | 1/2002 |
| WO | WO 01/080796 A1 | 10/2002 |
| WO | WO 02/080783 | 10/2002 |
| WO | WO02/080783 | 10/2002 |
| WO | WO02/080784 | 10/2002 |
| WO | WO 02/080784 | 10/2002 |
| WO | WO 02/080785 | 10/2002 |
| WO | WO02/080785 | 10/2002 |
| WO | WO02/080786 | 10/2002 |
| WO | WO 02/080786 | 10/2002 |
| WO | WO 02/080793 | 10/2002 |
| WO | WO02/080793 | 10/2002 |
| WO | WO 02/080794 | 10/2002 |
| WO | WO02/080794 | 10/2002 |
| WO | WO 02/080795 | 10/2002 |
| WO | WO 02/080796 | 10/2002 |
| WO | WO02/080797 | 10/2002 |
| WO | WO 02/080797 | 10/2002 |
| WO | WO 02/080798 | 10/2002 |
| WO | WO 02/080799 | 10/2002 |
| WO | WO 02/081170 | 10/2002 |
| WO | WO02/081170 | 10/2002 |
| WO | WO 03/101311 | 12/2003 |
| WO | WO 04/032777 | 4/2004 |
| WO | WO2004/032777 | 4/2004 |
| WO | WO 2004/052221 A1 | 6/2004 |
| WO | WO 04/073490 | 9/2004 |
| WO | WO2004/073490 | 9/2004 |
| WO | WO2004/073753 | 9/2004 |
| WO | WO 2004/082495 | 9/2004 |
| WO | WO 2004/082495 A1 | 9/2004 |
| WO | WO 2004/098383 A1 | 11/2004 |

| | | |
|---|---|---|
| WO | WO 04/103156 | 12/2004 |
| WO | WO2005/004735 | 1/2005 |

OTHER PUBLICATIONS

Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrholdectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics Figo World Congress 2000, Washington, D.C.
Crawford et al. "Use of the LigaSure Vessel Sealing System in Urologic Cancer Surger" Grand Rounds in Urology 1999 vol. 1 Issue 4 pp. 10-17.
Rothenberg et al. "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
Chung et al., "Clinical Experiance of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, □Apr. 2001 pp. 236-237.
Michael Choti, "Abdominoperineal Resection with the LigaSure Nessel Sealing System and LigaSure Atlas 20 cm Open Instrument" Innovations That Work, □Jun. 2003.
Craig Johnson, "Use of the LigaSure Vessel Sealing System in Bloodless Hemorrhoidectomy" Innovations That Work, □Mar. 2000.
Muller et al., "Extended Left Hemicolectomy Using the LigaSure Vessel Sealing System" Innovations That Work,□Sep. 1999.
Herman et al., "Laparoscopic Intestinal Resection With the LigaSure Vessel Sealing System: A Case Report" Innovations That Work,□2002.
Carus et al., "Initial Experience With The LigaSure Vessel Sealing System in Abnominal Surgery" Innovations That Work,□Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al., "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
Sengupta et al., "Use of a Computer-Controlled Bipolar Diathermy System in Radical Prostatectomies and Other Open Urological Surgery" ANZ Journal of Surgery (2001) 71.9 pp. 538-540.
PCT/US01/11340 International Search Report.
PCT/US01/11420 International Search Report.
PCT/US02/01890 International Search Report.
PCT/US02/11100 International Search Report.

PCT/US04/03436 International Search Report.
PCT/US04/13273 International Search Report.
PCT/US04/15311 International Search Report.
EP 98944778 International Search Report.
EP 98958575 International Search Report.
EP 04027479 International Search Report.
EP 04027705 International Search Report.
EP 04027314 International Search Report.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Olsson et al. "Radical Cystectomy in Females" Current Surgical Techniques in Urology, vol. 14, Issue 3, 2001.
Dulemba et al. "Use of a Bipolar Electrothermal Vessel Sealer in Laparoscopically Assisted Vaginal Hysterectomy" Sales Product Literature; Jan. 2004.
Johnson et al. "Evaluation of a Bipolar electrothermal Vessel Sealing Device in Hemorrhoidectomy" Sales Product Literature; Jan. 2004.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021779.8 dated Jan. 31, 2006.
Int'l Search Report EP 05021937.7 dated Jan. 13, 2006.
Int'l Search Report—extended- EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
PCT/US01/11340 International Search Report, Aug. 2001.
PCT/US01/11420 International Search Report, Oct. 2001.
PCT/US02/01890 International Search Report, Jul. 2002.
PCT/US02/11100 International Search Report, Jul. 2002.
PCT/US04/03436 International Search Report, Mar. 2005.
PCT/US04/13273 International Search Report, Dec. 2004.
PCT/US04/15311 International Search Report, Jan. 2005.
EP 98944778 International Search Report, Nov. 2000.
EP 98958575 International Search Report, Oct. 2002.
EP 04027479 International Search Report, Mar. 2005.
EP 04027705 International Search Report, Feb. 2005.
EP 04027314 International Search Report, Mar. 2005.
Joseph Ortenberg "LigaSure System Used in Laparoscopic 1st and 2nd Stage Orchiopexy" Innovations That Work, Nov. 2002.
Koyle et al., "Laparoscopic Palomo Varicocele Ligation in Children and Adolescents" Pediatric Endosurgery & Innovative Techniques, vol. 6, No. 1, 2002.
Int'l Search Report PCT/US01/11218, Aug. 2001.
Int'l Search Report PCT/US99/24869, Feb. 2000.
Int'l Search Report PCT/US98/18640, Jan. 1999.
Int'l Search Report PCT/US98/23950, Jan. 1999.
Levy et al. "Use of a New Energy-based Vessel Ligation Device During Vaginal Hysterectomy" Int'l Federation of Gynecology and Obstetrics (FIGO) World Congress 1999.
"Reducing Needlestick Injuries in the Operating Room" Sales/Product Literature 2001.
W. Scott Helton, "LigaSure Vessel Sealing System: Revolutionary Hemostasis Product for General Surgery" Sales/Product Literature 1999.
McLellan et al. "Vessel Sealing For Hemostasis During Gynecologic Surgery" Sales/Product Literature 1999.

E. David Crawford "Use of a Novel Vessel Sealing Technology in Management of the Dorsal Veinous Complex" Sales/Product Literature 2000.

Jarrett et al., "Use of the LigaSure Vessel Sealing System for Peri-Hilar Vessels in Laparoscopic Nephrectomy" Sales/Product Literature 2000.

E. David Crawford "Evaluation of a New Vessel Sealing Device in Urologic Cancer Surgery" Sales/Product Literature 2000.

Int'l Search Report EP 04013772 dated Apr. 1, 2005.

Int'l Search Report EP 05013895 dated Oct. 14, 2005.

Int'l Search Report EP 05017281 dated Nov. 16, 2005.

Int'l Search Report EP 06006716 dated Aug. 4, 2006.

Int'l Search Report PCT/US01/11224 dated Nov. 13, 2001.

Int'l Search Report EP 06014461.5 dated Oct. 20, 2006.

Int'l Search Report EP 06020584.6 dated Jan. 12, 2007.

Int'l Search Report EP 06020583.8 dated Jan. 30, 2007.

Int'l Search Report EP 06020756.0 dated Feb. 5, 2007.

Int'l Search Report EP 06024123.9 dated Feb. 26, 2007.

* cited by examiner

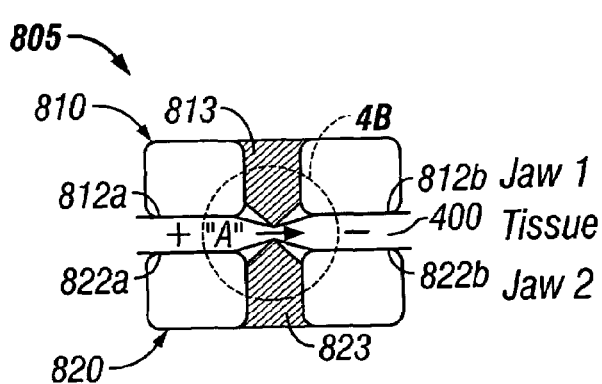
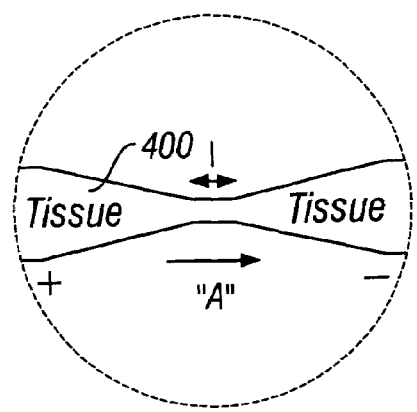
FIG. 4A
FIG. 4B
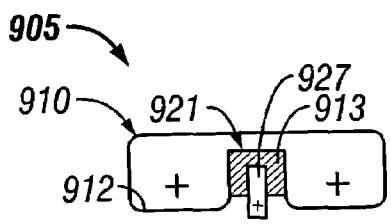
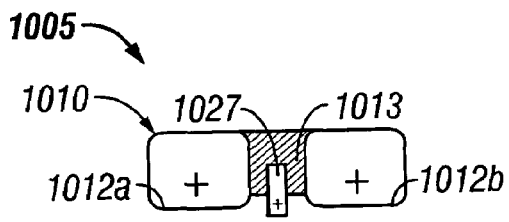
FIG. 4C
FIG. 4D
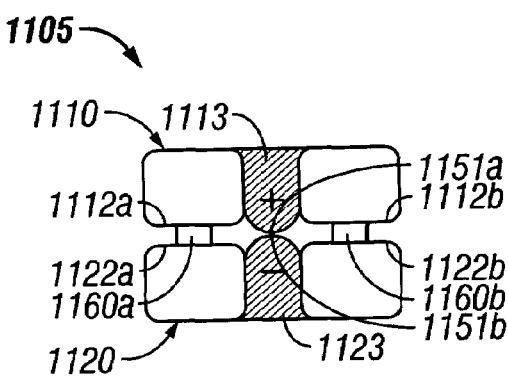
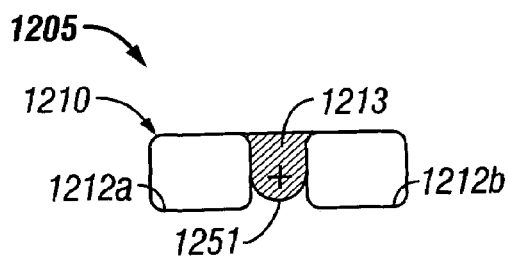
FIG. 4E
FIG. 4F
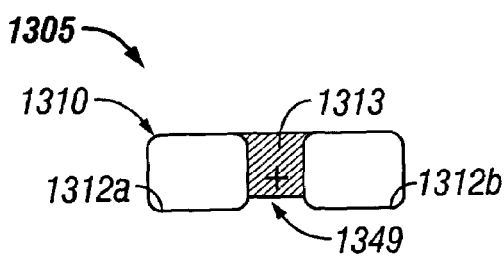
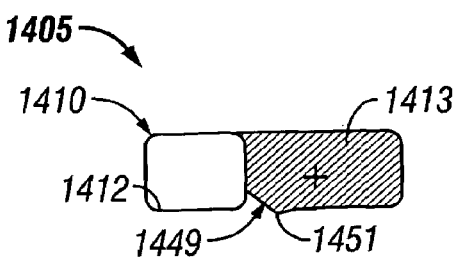
FIG. 4G
FIG. 4H

VESSEL SEALING INSTRUMENT WITH ELECTRICAL CUTTING MECHANISM

CROSS REFERENCE TO RELATED APPLICATION

This application claims the benefits of and is a continuation-in-part of PCT Application Serial No. PCT/US03/28539 filed on Sep. 11, 2003 entitled "ELECTRODE ASSEMBLY FOR SEALING AND CUTTING TISSUE AND METHOD FOR PERFORMING SAME" which claims the benefit of priority to U.S. Provisional Application Ser. No. 60/416,064 filed on Oct. 4, 2002 entitled "ELECTRODE ASSEMBLY FOR SEALING AND CUTTING TISSUE AND METHOD FOR PERFORMING SAME" the entire contents of both which being incorporated by reference herein.

BACKGROUND

The present disclosure relates to a forceps used for both endoscopic and open surgical procedures which includes an electrode assembly which allows a user to selectively seal and/or cut tissue. More particularly, the present disclosure relates to a forceps which includes a first set of electrically conductive surfaces which applies a unique combination of mechanical clamping pressure and electrosurgical energy to effectively seal tissue and a second set of electrically conductive surfaces which is selectively energizable to sever tissue between sealed tissue areas.

TECHNICAL FIELD

Open or endoscopic electrosurgical forceps utilize both mechanical clamping action and electrical energy to effect hemostasis. The electrode of each opposing jaw member is charged to a different electric potential such that when the jaw members grasp tissue, electrical energy can be selectively transferred through the tissue. A surgeon can either cauterize, coagulate/desiccate and/or simply reduce or slow bleeding, by controlling the intensity, frequency and duration of the electrosurgical energy applied between the electrodes and through the tissue.

Certain surgical procedures require more than simply cauterizing tissue and rely on the combination of clamping pressure, electrosurgical energy and gap distance to "seal" tissue, vessels and certain vascular bundles. More particularly, vessel sealing or tissue sealing is a recently-developed technology which utilizes a unique combination of radiofrequency energy, clamping pressure and precise control of gap distance (i.e., distance between opposing jaw members when closed about tissue) to effectively seal or fuse tissue between two opposing jaw members or sealing plates. Vessel or tissue sealing is more than "cauterization" which involves the use of heat to destroy tissue (also called "diathermy" or "electrodiathermy"). Vessel sealing is also more than "coagulation" which is the process of desiccating tissue wherein the tissue cells are ruptured and dried. "Vessel sealing" is defined as the process of liquefying the collagen, elastin and ground substances in the tissue so that the tissue reforms into a fused mass with significantly-reduced demarcation between the opposing tissue structures.

To effectively seal tissue or vessels, especially thick tissue and large vessels, two predominant mechanical parameters must be accurately controlled: 1) the pressure applied to the vessel; and 2) the gap distance between the conductive tissue contacting surfaces (electrodes). As can be appreciated, both of these parameters are affected by the thickness of the vessel or tissue being sealed. Accurate application of pressure is important for several reasons: to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between about 0.001 and about 0.006 inches. Below this range, the seal may shred or tear and above this range the tissue may not be properly or effectively sealed.

With respect to smaller vessels, the pressure applied becomes less relevant and the gap distance between the electrically conductive surfaces becomes more significant for effective sealing. In other words, the chances of the two electrically conductive surfaces touching during activation increases as the tissue thickness and the vessels become smaller.

Typically and particularly with respect to endoscopic electrosurgical procedures, once a vessel is sealed, the surgeon has to remove the sealing instrument from the operative site, substitute a new instrument through the cannula and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue seal.

Several attempts have been made to design an instrument which incorporates a knife or blade member which effectively severs the tissue after forming a tissue seal. For example, U.S. Pat. No. 5,674,220 to Fox et al. discloses a transparent instrument which includes a longitudinally reciprocating knife which severs the tissue once sealed. The instrument includes a plurality of openings which enable direct visualization of the tissue during the treatment and severing processes. This direct visualization allows a user to visually and manually regulate the closure force and gap distance between jaw members to reduce and/or limit certain undesirable visual effects known to occur when treating vessels, thermal spread, charring, etc. As can be appreciated, the overall success of creating an effective tissue seal with this instrument is greatly reliant upon the user's expertise, vision, dexterity, and experience in judging the appropriate closure force, gap distance and length of reciprocation of the knife to uniformly, consistently and effectively seal the vessel and separate the tissue at the seal along an ideal cutting plane.

U.S. Pat. No. 5,702,390 to Austin et al. discloses an instrument which includes a triangularly-shaped electrode which is rotatable from a first position to treat tissue to a second position to cut tissue. Again, the user must rely on direct visualization and expertise to control the various effects of treating and cutting tissue.

Thus, a need exists to develop an electrosurgical instrument which includes an electrode assembly which enables the surgeon to both seal the tissue in an effective and consistent manner and subsequently separate the tissue along the tissue seal without re-grasping the tissue or removing the instrument from the operating cavity.

SUMMARY

The present disclosure relates to an end effector assembly for use with an instrument for sealing vessel and cutting vessels and/or tissue and includes a pair of opposing first and second jaw members which are movable relative to one another from a first position wherein the jaw members are disposed in spaced relation relative to one another to a second position wherein the jaw members cooperate to grasp vessels/tissue therebetween. Preferably, each jaw member includes a pair of spaced apart, electrically conductive vessel/tissue sealing surfaces extending along a length thereof. Each pair of vessel/tissue sealing surfaces is connected to a source of electrosurgical energy such that the vessel/tissue sealing surfaces are capable of conducting electrosurgical energy through vessels/tissue held therebetween to effect a vessel/tissue seal.

The end effector assembly also includes an insulator disposed between each pair of electrically conductive sealing surfaces. In one embodiment according to the present disclosure, at least one of the insulators is configured to at least partially extend to a position which is at least substantially flush with the cutting element. In yet another embodiment, a second electrically conductive cutting element is disposed within the insulator of the second jaw member which opposes the first electrically conductive cutting element. In this instance, the first and second electrically conductive cutting elements when disposed on opposite sides of tissue form the gap distance between electrically conductive sealing surfaces when the jaw members are disposed in the second position.

The first jaw member includes an electrically conductive cutting element disposed within the insulator of the first jaw member which is disposed in general vertical registration with the insulator on the second jaw member. The cutting element extends from the first electrically conductive sealing surface towards the second electrically conductive sealing surface and is configured to create a gap between the electrically conductive sealing surfaces when the jaw members are disposed in the second position for sealing vessel/tissue. The cutting element is inactive during the sealing process while the pair of spaced apart electrically conductive sealing surfaces on the first jaw member are energized to a different potential from the corresponding pair of spaced apart electrically conductive sealing surfaces on the second jaw member such that electrosurgical energy can be transferred through the tissue to effect a vessel/tissue seal.

The end effector assembly is designed such that the cutting element is energized to a first potential during the cutting process and at least one electrically conductive sealing surface on the first jaw member and at least one electrically conductive sealing surface on the second jaw member are energized to a different potential such that electrosurgical energy can be transferred through the vessels/tissue to effect a vessel/tissue cut.

Preferably, the cutting element and sealing processes are automatically controlled by an electrosurgical energy source. In one embodiment according to the present disclosure, it is envisioned that the potential of the electrically conductive sealing surface of the first jaw member and the potential of the cutting element are independently activatable by the surgeon. In another embodiment, the electrical potential of the cutting element and the electrical potential of at least one electrically conductive sealing surface are automatically configured for cutting when the surgeon selectively activates a trigger. Preferably, the cutting element is substantially dull and only capable of cutting vessels/tissue through electrosurgical activation.

In yet another embodiment according to the present disclosure a smart sensor is included for determining seal quality prior to cutting. The smart sensor may include either an audible or visual indicator for indicating seal quality. Preferably, the smart sensor automatically switches electrosurgical energy to the cutting element once the vessel/tissue is sealed.

In still yet another embodiment of the end effector assembly according to the present disclosure a first switch is included for energizing the electrically conductive sealing surfaces to effect vessel/tissue sealing and a trigger is included for energizing the cutting element and at least one of the electrically conductive sealing surfaces to effect vessel/tissue cutting.

Another embodiment according to the present disclosure includes an end effector assembly for use with an instrument for sealing and/or cutting vessels or tissue which includes a pair of opposing first and second jaw members which movable relative to one another from a first position wherein the jaw members are disposed in spaced relation relative to one another to a second position wherein the jaw members cooperate to grasp vessel/tissue therebetween. Each jaw member of the end effector assembly includes a pair of spaced apart, electrically conductive sealing surfaces which extend along a length thereof. Each sealing surface is connected to a source of electrosurgical energy such that the sealing surfaces are capable of conducting electrosurgical energy through vessel/tissue held therebetween to effect a vessel/tissue seal. The end effector assembly further includes an insulator disposed between each pair of electrically conductive sealing surfaces.

Preferably, the first jaw member includes an electrically conductive cutting element disposed within or disposed on the insulator of the first jaw member, the electrically conductive cutting element is disposed in general vertical registration to the insulator on the second jaw member. At least one stop member is included which is operatively associated with one of the first and second jaw members and is dimensioned to create a gap between the electrically conductive sealing surfaces when the jaw members close for sealing vessel/tissue.

Preferably, the cutting element is inactive during the sealing process and the pair of spaced apart electrically conductive sealing surfaces on the first jaw member are energized to a different potential from the corresponding pair of spaced apart electrically conductive sealing surfaces on the second jaw member such that electrosurgical energy can be transferred through the vessel/tissue to effect a vessel/tissue seal. During the cutting process, the cutting element is energized to a first potential and at least one electrically conductive sealing surface on the first jaw member and at least one electrically conductive sealing surface on the second jaw member are energized to a different potential such that electrosurgical energy can be transferred through the vessel/tissue to effect a vessel/tissue cut.

BRIEF DESCRIPTION OF THE DRAWINGS

Various embodiments of the subject instrument are described herein with reference to the drawings wherein:

FIG. 4A is an enlarged, schematic end view showing one electrode assembly configuration with tissue disposed between the jaw members;

FIG. 4B is a schematic end view showing the area of detail of FIG. 4A;

FIGS. 4C-4J are enlarged, schematic end views showing various configurations for an upper jaw member to promote electrical cutting;

DETAILED DESCRIPTION

Figure 1A:
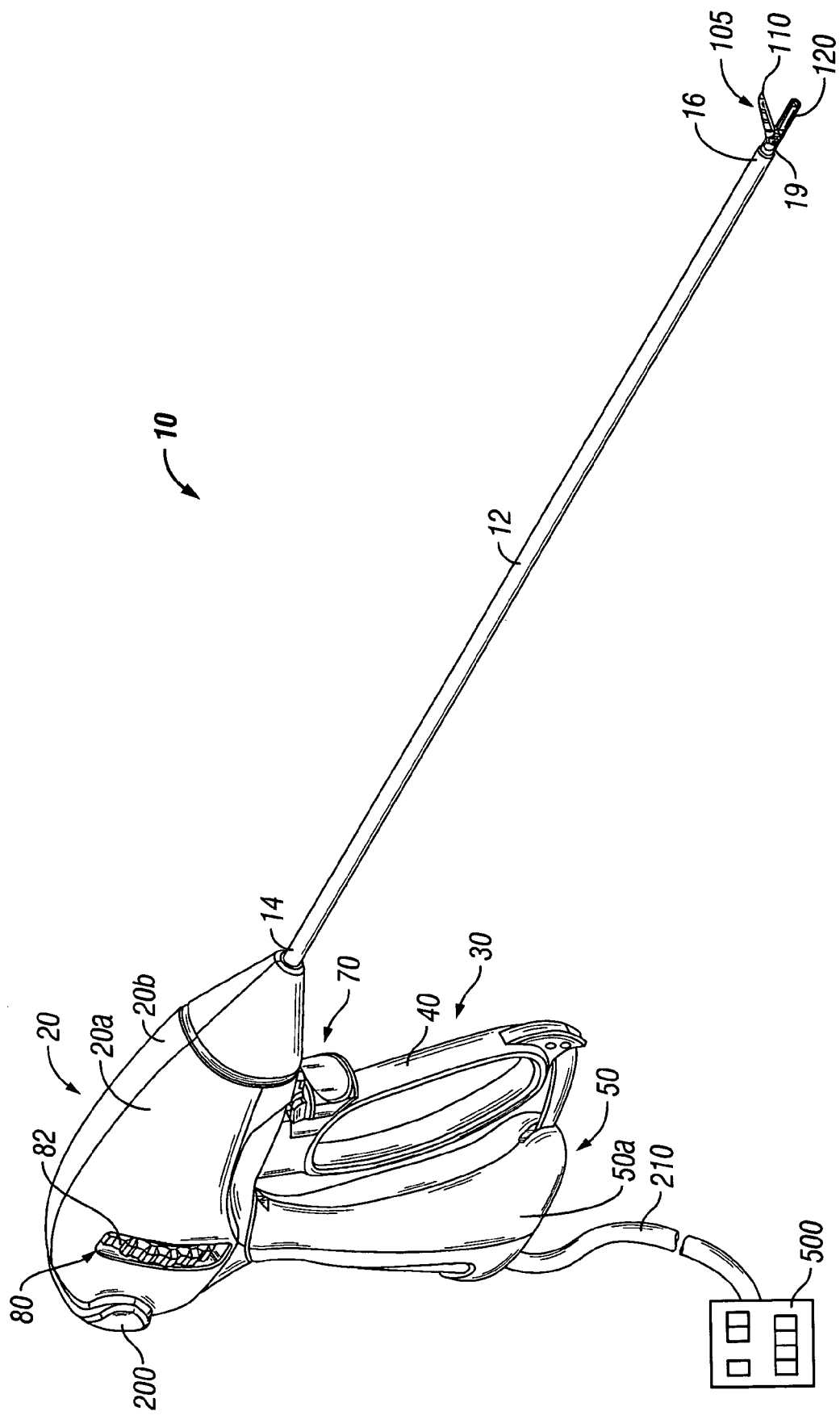
FIG. 1A is a right, perspective view of an endoscopic bipolar forceps having a housing, a shaft and a pair of jaw members affixed to a distal end thereof, the jaw members including an electrode assembly disposed therebetween.

For the purposes herein, vessel/tissue cutting or vessel/tissue division is believed to occur when heating of the vessel/tissue leads to expansion of intracellular and/or extracellular fluid, which may be accompanied by cellular vaporization, desiccation, fragmentation, collapse and/or shrinkage along a so-called "cut zone" in the vessel/tissue. By focusing the electrosurgical energy and heating in the cut zone, the cellular reactions are localized creating a fissure. Localization is achieved by regulating the vessel/tissue condition and energy delivery which may be controlled by utilizing one or more of the various geometrical electrode and insulator configurations described herein. The cut process may also be controlled by utilizing a generator and feedback algorithm (and one or more of the hereindescribed geometrical configurations of the electrode and insulator assemblies) which increases the localization and maximizes the so-called "cutting effect".

For example, it is envisioned that the below described factors contribute and/or enhance vessel/tissue division using electrosurgical energy. Each of the factors described below may be employed individually or in any combination to achieve a desired cutting effect. For the purposes herein the term "cut effect" or "cutting effect" refers to the actual division of tissue by one or more of the electrical or electromechanical methods or mechanisms described below. The term "cutting zone" or "cut zone" refers to the region of vessel/tissue where cutting will take place. The term "cutting process" refers to steps that are implemented before, during and/or after vessel/tissue division that tend to influence the vessel/tissue as part of achieving the cut effect.

For the purposes herein the terms "tissue" and "vessel" may be used interchangeably since it is believed that the present disclosure may be employed to seal and cut tissue or seal and cut vessels utilizing the same inventive principles described herein.

It is believed that the following factors either alone or in combination, play an important role in dividing tissue:

Localizing or focusing electrosurgical energy in the cut zone during the cutting process while minimizing energy effects to surrounding tissues;

Focusing the power density in the cut zone during the cutting process;

Creating an area of increased temperature in the cut zone during the cutting process (e.g., heating that occurs within the tissue or heating the tissue directly with a heat source);

Pulsing the energy delivery to influence the tissue in or around the cut zone. "Pulsing" involves as a combination of an "on" time and "off" time during which the energy is applied and then removed repeatedly at any number of intervals for any amount of time. The pulse "on" and "off" time may vary between pulses. The pulse "on" typically refers to a state of higher power delivery and pulse "off" typically refers to a state of lower power delivery;

Spiking the energy delivery creates a momentary condition of high energy application with an intent to influence the tissue in or around the cut zone during the cut process. The momentary condition may be varied to create periods of high energy application;

Conditioning the tissue before or during the cutting process to create more favorable tissue conditions for cutting. This includes tissue pre-heating before the cutting processes and tissue rehydration during the cutting process;

Controlling the tissue volume in or around the cut zone to create more favorable conditions for tissue cutting;

Controlling energy and power delivery to allow vaporization to enhance and or contribute to the cutting process. For example, controlling the energy delivery to vaporize both intracellular and/or extracellular fluids and/or other cellular materials and foreign fluids within the cut zone;

Fragmenting the tissue or cellular material during the cutting process to enhance tissue division in the cut zone;

Melting or collapsing the tissue or cellular material during the cutting process to enhance tissue division in the cut zone. For example, melting the tissue to create internal stress within the tissue to induce tissue tearing;

Controlling tissue temperature, arcing, power density and/or current density during the cutting process to enhance tissue division in the cut zone;

Applying various mechanical elements to the tissue such as pressure, tension and/or stress (either internally or externally) to enhance the cutting process; and Utilizing various other tissue treatments before or during the cutting process to enhance tissue cutting, e.g., tissue sealing, cauterization and/or coagulation.

Many of the electrode assemblies described herein employ one or more of the above-identified factors for enhancing tissue division. For example, many of the electrode assemblies described herein utilize various geometrical configurations of electrodes, cutting elements, insulators, partially conductive materials and semiconductors to produce or enhance the cutting effect. In addition, by controlling or regulating the electrosurgical energy from the generator in any of the ways described above, tissue cutting may be initiated, enhanced or facilitated within the tissue cutting zone. For example, it is believed that the geometrical configuration of the electrodes and insulators may be configured to produce a so-called "cut effect" which may be directly related to the amount of vaporization or fragmentation at a point in the tissue or the power density, temperature density and/or mechanical stress applied to a point in the tissue. The geometry of the electrodes may be configured such that the surface area ratios between the electrical poles focus electrical energy at the tissue. Moreover, it is envisioned that the geometrical configurations of the electrodes and insulators may be designed such that they act like electrical sinks or insulators to influence the heat effect within and around the tissue during the sealing or cutting processes.

Figure 1B:
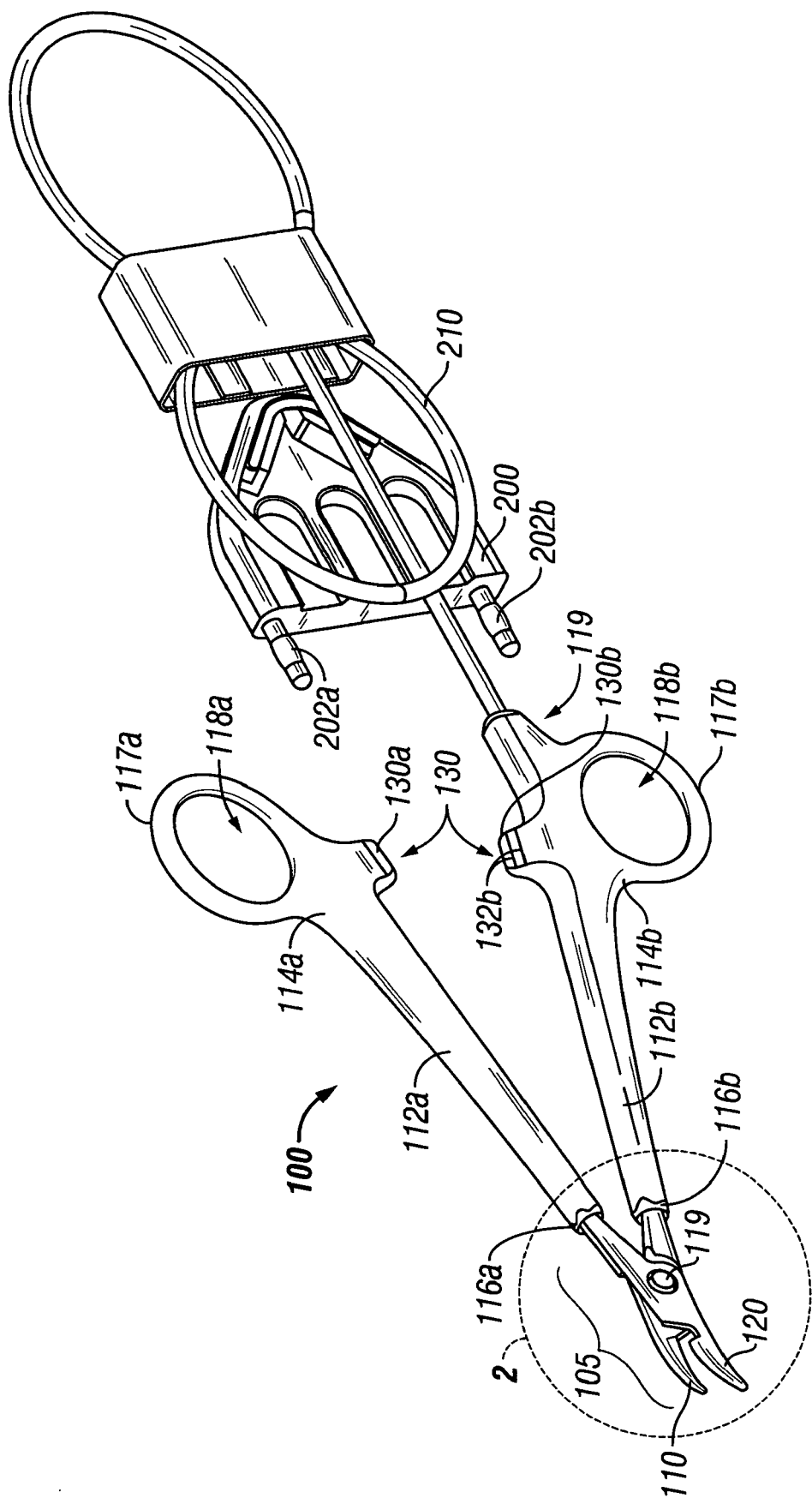
FIG. 1B is a left, perspective view of an open bipolar forceps showing a pair of first and second shafts each having a jaw member affixed to a distal end thereof with an electrode assembly disposed therebetween.

Referring now to FIGS. 1A and 1B, FIG. 1A depicts a bipolar forceps 10 for use in connection with endoscopic surgical procedures and FIG. 1B depicts an open forceps 100 contemplated for use in connection with traditional open surgical procedures. For the purposes herein, either an endoscopic instrument or an open instrument may be utilized with the electrode assembly described herein. Obviously, different electrical and mechanical connections and considerations apply to each particular type of instrument, however, the novel aspects with respect to the electrode assembly and its operating characteristics remain generally consistent with respect to both the open or endoscopic designs.

FIG. 1A shows a bipolar forceps 10 for use with various endoscopic surgical procedures and generally includes a housing 20, a handle assembly 30, a rotating assembly 80, a switch assembly 70 and an electrode assembly 105 having opposing jaw members 110 and 120 which mutually cooperate to grasp, seal and divide tubular vessels and vascular tissue. More particularly, forceps 10 includes a shaft 12 which has a distal end 16 dimensioned to mechanically engage the electrode assembly 105 and a proximal end 14 which mechanically engages the housing 20. The shaft 12 may include one or more known mechanically engaging components which are designed to securely receive and engage the electrode assembly 105 such that the jaw members 110 and 120 are pivotable relative to one another to engage and grasp tissue therebetween.

The proximal end 14 of shaft 12 mechanically engages the rotating assembly 80 (not shown) to facilitate rotation of the electrode assembly 105. In the drawings and in the descriptions which follow, the term "proximal", as is traditional, will refer to the end of the forceps 10 which is closer to the user, while the term "distal" will refer to the end which is further from the user. Details relating to the mechanically cooperating components of the shaft 12 and the rotating assembly 80 are described in commonly-owned U.S. patent application Ser. No. 10/460,926 entitled "VESSEL SEALER AND DIVIDER FOR USE WITH SMALL TROCARS AND CANNULAS" filed on Jun. 13, 2003 the entire contents of which are incorporated by reference herein.

Handle assembly 30 includes a fixed handle 50 and a movable handle 40. Fixed handle 50 is integrally associated with housing 20 and handle 40 is movable relative to fixed handle 50 to actuate the opposing jaw members 110 and 120 of the electrode assembly 105 as explained in more detail below. Movable handle 40 and switch assembly 70 are preferably of unitary construction and are operatively connected to the housing 20 and the fixed handle 50 during the assembly process. Housing 20 is preferably constructed from two components halves 20a and 20b which are assembled about the proximal end of shaft 12 during assembly. Switch assembly is configured to selectively provide electrical energy to the electrode assembly 105.

As mentioned above, electrode assembly 105 is attached to the distal end 16 of shaft 12 and includes the opposing jaw members 110 and 120. Movable handle 40 of handle assembly 30 imparts movement of the jaw members 110 and 120 from an open position wherein the jaw members 110 and 120 are disposed in spaced relation relative to one another, to a clamping or closed position wherein the jaw members 110 and 120 cooperate to grasp tissue therebetween.

Referring now to FIG. 1B, an open forceps 100 includes a pair of elongated shaft portions 112a and 112b each having a proximal end 114a and 114b, respectively, and a distal end 116a and 116b, respectively. The forceps 100 includes jaw members 120 and 110 which attach to distal ends 116a and 116b of shafts 112a and 112b, respectively. The jaw members 110 and 120 are connected about pivot pin 119 which allows the jaw members 110 and 120 to pivot relative to one another from the first to second positions for treating tissue. The electrode assembly 105 is connected to opposing jaw members 110 and 120 and may include electrical connections through or around the pivot pin 119. Examples of various electrical connections to the jaw members are shown in commonly-owned U.S. patent application Ser. Nos. 10/474,170, 10/116,824, 10/284,562 10/472,295, 10/116,944, 10/179,863 and 10/369,894, the contents of all of which are hereby incorporated by reference herein.

Preferably, each shaft 112a and 112b includes a handle 117a and 117b disposed at the proximal end 114a and 114b thereof which each define a finger hole 118a and 118b, respectively, therethrough for receiving a finger of the user. As can be appreciated, finger holes 118a and 118b facilitate movement of the shafts 112a and 112b relative to one another which, in turn, pivot the jaw members 110 and 120 from the open position wherein the jaw members 110 and 120 are disposed in spaced relation relative to one another to the clamping or closed position wherein the jaw members 110 and 120 cooperate to grasp tissue therebetween. A ratchet 130 is preferably included for selectively locking the jaw members 110 and 120 relative to one another at various positions during pivoting.

More particularly, the ratchet 130 includes a first mechanical interface 130a associated with shaft 112a and a second mating mechanical interface associated with shaft 112b. Preferably, each position associated with the cooperating ratchet interfaces 130a and 130b holds a specific, i.e., constant, strain energy in the shaft members 112a and 112b which, in turn, transmits a specific closing force to the jaw members 110 and 120. It is envisioned that the ratchet 130 may include graduations or other visual markings which enable the user to easily and quickly ascertain and control the amount of closure force desired between the jaw members 110 and 120.

As best seen in FIG. 1B, forceps 100 also includes an electrical interface or plug 200 which connects the forceps 100 to a source of electrosurgical energy, e.g., an electrosurgical generator (not shown). Plug 200 includes at least two prong members 202a and 202b which are dimensioned to mechanically and electrically connect the forceps 100 to the electrosurgical generator 500 (See FIG. 1A). An electrical cable 210 extends from the plug 200 and securely connects the cable 210 to the forceps 100. Cable 210 is internally divided within the shaft 112b to transmit electrosurgical energy through various electrical feed paths to the electrode assembly 105.

One of the shafts, e.g., 112b, includes a proximal shaft connector/flange 119 which is designed to connect the forceps 100 to a source of electrosurgical energy such as an electrosurgical generator 500. More particularly, flange 119 mechanically secures electrosurgical cable 210 to the forceps 100 such that the user may selectively apply electrosurgical energy as needed.

Figure 2:
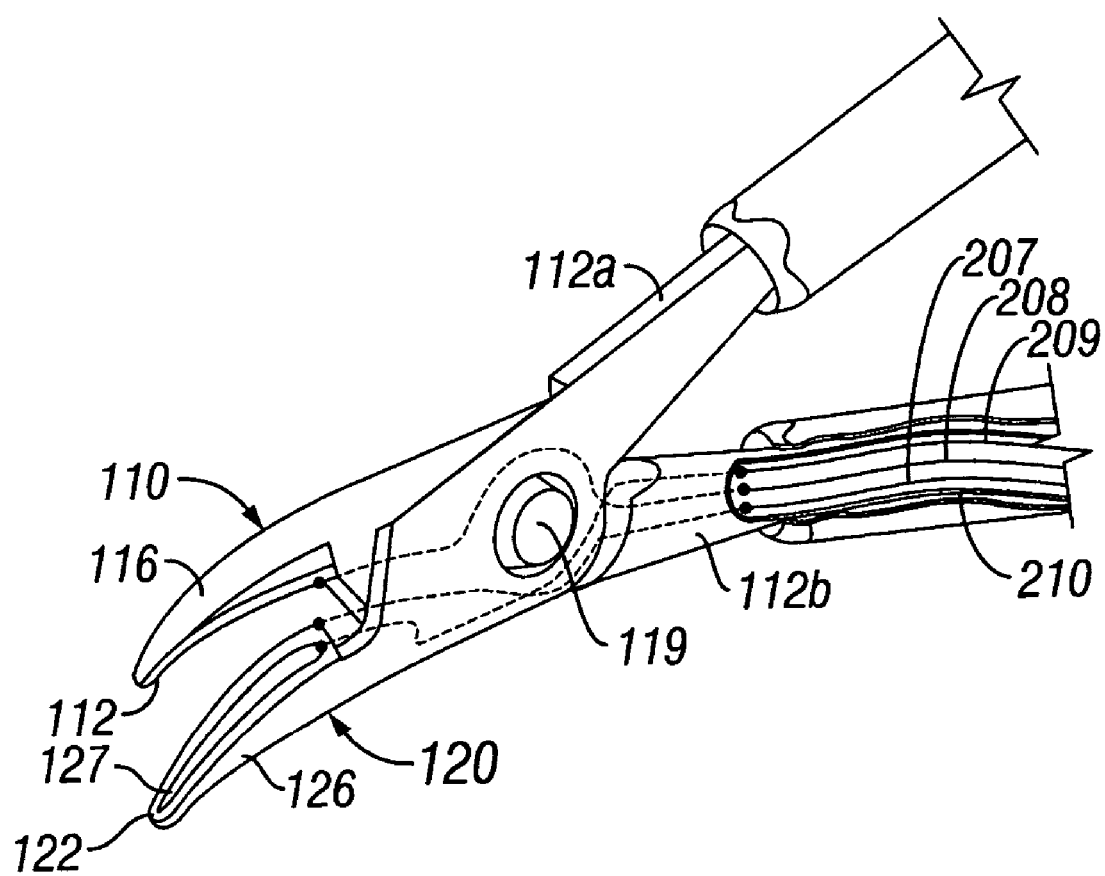
FIG. 2 is an enlarged view of the area of detail of FIG. 1B

As best shown in the schematic illustration of FIG. 2, the jaw members 110 and 120 of both the endoscopic version of FIG. 1A and the open version of FIG. 1B are generally symmetrical and include similar component features which cooperate to permit facile rotation about pivot 19, 119 to effect the grasping and sealing of tissue. Each jaw member 110 and 120 includes an electrically conductive tissue contacting surface 112 and 122, respectively, which cooperate to engage the tissue during sealing and cutting. At least one of the jaw members, e.g., jaw member 120, includes a electrically energizable cutting element 127 disposed therein which is explained in detail below. Together and as shown in the various figure drawings described hereafter, the electrode assembly 105 includes the combination of the sealing electrodes 112 and 122 and the cutting element(s) 127.

The various electrical connections of the electrode assembly 105 are preferably configured to provide electrical continuity to the tissue contacting surfaces 110 and 120 and the cutting element(s) 127 through the electrode assembly 105. For example, cable lead 210 may be configured to include three different leads, namely, leads 207, 208 and 209 which carry different electrical potentials. The cable leads 207, 208 and 209 are fed through shaft 112b and connect to various electrical connectors (not shown) disposed within the proximal end of the jaw member 110 which ultimately connect to the electrically conductive sealing surfaces 112 and 122 and cutting element(s) 127. As can be appreciated, the electrical connections may be permanently soldered to the shaft 112b during the assembly process of a disposable instrument or, alternatively, selectively removable for use with a reposable instrument. Commonly owned U.S. patent application Ser. Nos. 10/474,170, 10/116,824 and 10/284,562 all disclose various types of electrical connections which may be made to the jaw members 110 and 120 through the shaft 112b the contents of all of which being hereby incorporated by reference wherein. In addition and with respect to the types of electrical connections which may be made to the jaw members 110 and 120 for endoscopic purposes, commonly-owned U.S. patent application Ser. Nos. 10/472,295, 10/116,944, 10/179,863 and 10/369,894 all disclose other types of electrical connections which are hereby incorporated by reference herein in their entirety.

The various electrical connections from lead 210 are preferably dielectrically insulated from one another to allow selective and independent activation of either the tissue contacting surfaces 112 and 122 or the cutting element 127 as explained in more detail below. Alternatively, the electrode assembly 105 may include a single connector which includes an internal switch (not shown) to allow selective and independent activation of the tissue contacting surfaces 112, 122 and the cutting element 127. Preferably, the leads 207, 208 and 209 (and/or conductive pathways) do not encumber the movement of the jaw members 110 and 120 relative to one another during the manipulation and grasping of tissue. Likewise, the movement of the jaw members 110 and 120 do not unnecessarily strain the lead connections.

Figure 3A:
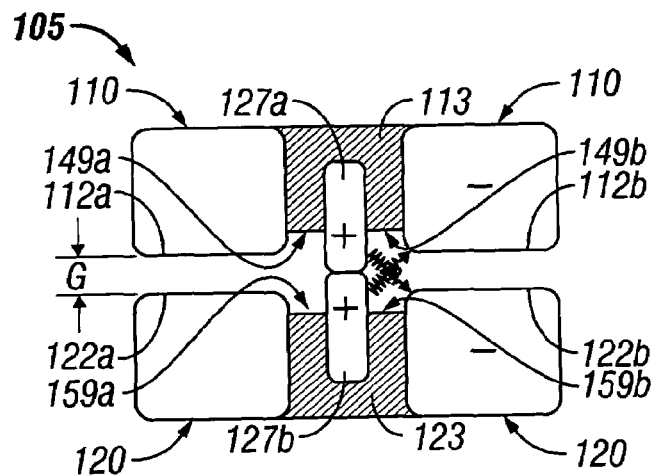
FIGS. 3A-3F are enlarged, schematic end views showing a variety of different electrode assemblies according to the present disclosure with electrical potentials identified for electrical cutting.
Figure 3B:
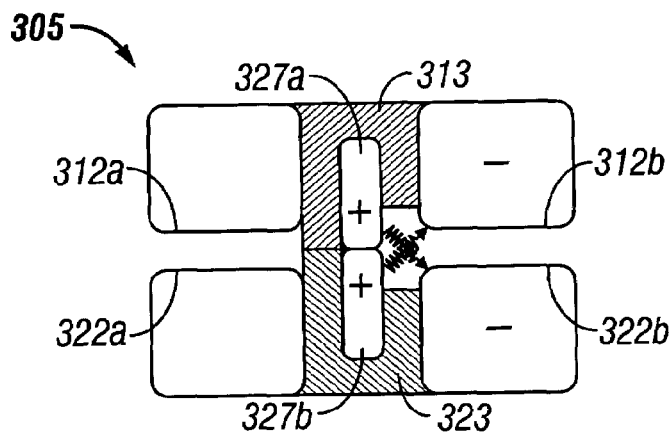
Figure 3C:
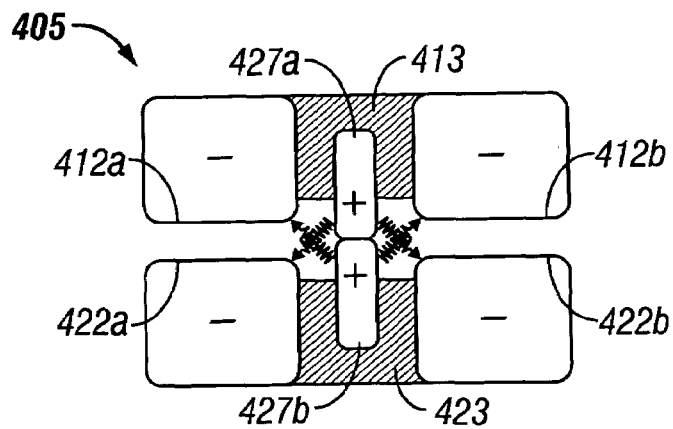
Figure 3D:
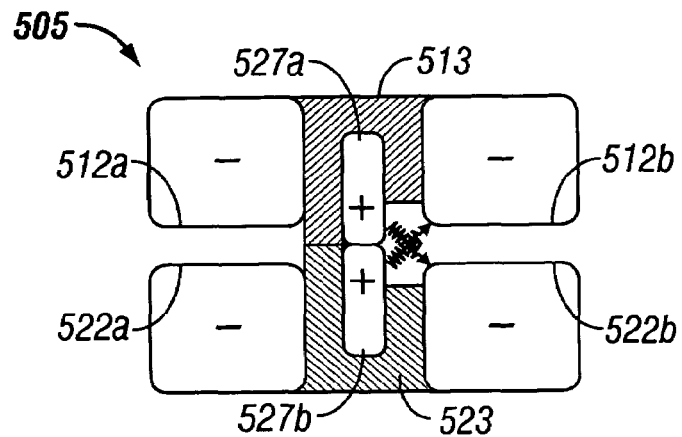
Figure 3E:
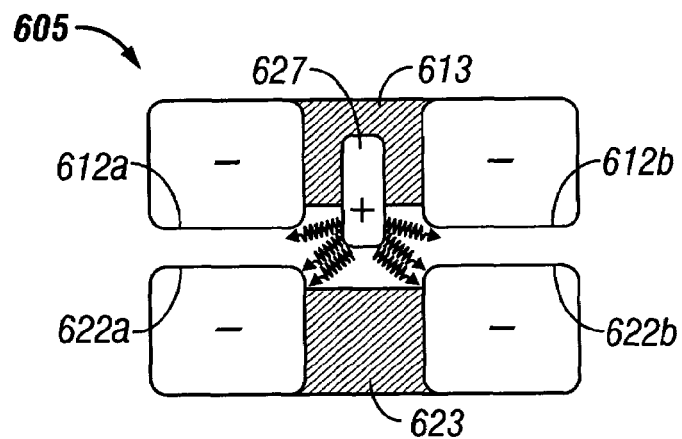
Figure 3F:
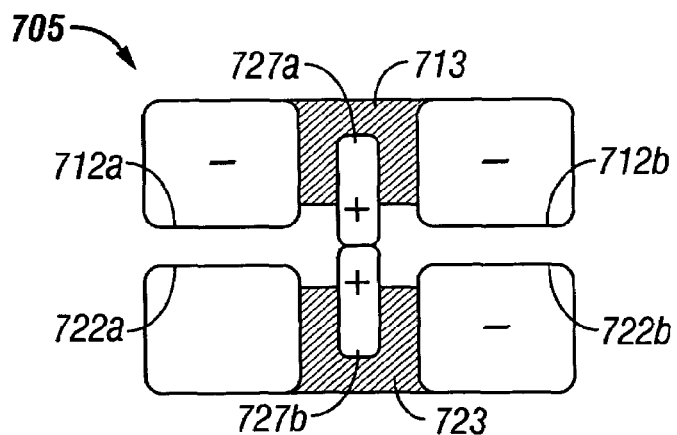

As best seen in FIGS. 2-3F, various electrical configurations of the electrode assembly 105 are shown which are designed to effectively seal and cut tissue disposed between the sealing surfaces 112 and 122 and the cutting elements 127 of the opposing jaw members 110 and 120, respectively. More particularly and with respect to FIGS. 2 and 3A, jaw members 110 and 120 include conductive tissue contacting surfaces 112 and 122, respectively, disposed along substantially the entire longitudinal length thereof (i.e., extending substantially from the proximal to distal end of the respective jaw member 110 and 120). It is envisioned that tissue contacting surfaces 112 and 122 may be attached to the jaw member 110, 120 by stamping, by overmolding, by casting, by overmolding a casting, by coating a casting, by overmolding a stamped electrically conductive sealing plate and/or by overmolding a metal injection molded seal plate or in other ways customary in the art. All of these manufacturing techniques may be employed to produce jaw member 110 and 120 having an electrically conductive tissue contacting surface 112 and 122 disposed thereon for contacting and treating tissue.

With respect to FIG. 3A, the jaw members 110 and 120 both include an insulator or insulative material 113 and 123, respectively, disposed between each pair of electrically conductive sealing surfaces on each jaw member 110 and 120, i.e., between pairs 112a and 112b and between pairs 122a and 122b. Each insulator 113 and 123 is generally centered between its respective tissue contacting surface 112a, 112b and 122a, 122b along substantially the entire length of the respective jaw member 110 and 120 such that the two insulators 113 and 123 generally oppose one another.

One or both of the insulators 113, 123 may be made from a ceramic material due to its hardness and inherent ability to withstand high temperature fluctuations. Alternatively, one or both of the insulators 113, 123 may be made from a material having a high Comparative Tracking Index (CTI) having a value in the range of about 300 to about 600 volts. Examples of high CTI materials include nylons and syndiotactic polystryrenes such as QUESTRA® manufactured by DOW Chemical. Other materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate.

At least one jaw member 110 and/or 120 includes an electrically conductive cutting element 127 disposed substantially within or disposed on the insulator 113, 123. As described in detail below, the cutting element 127 (in many of the embodiments described hereinafter) plays a dual role during the sealing and cutting processes, namely: 1) to provide the necessary gap distance between conductive surfaces 112a, 112b and 122a, 122b during the sealing process; and 2) to electrically energize the tissue along the previously formed tissue seal to cut the tissue along the seal. With respect to FIG. 3A, the cutting elements 127a, 127b are electrically conductive, however, it is envisioned that one or both of the cutting elements 127a, 127b may be made from an insulative material with a conductive coating disposed thereon or one (or both) of the cutting elements may be non-conductive (See, e.g., FIG. 4A). Preferably, the distance between the cutting element(s) 127a and the opposing cutting element 127b (or the opposing return electrode in some cases) is within the range of about 0.008 inches to about 0.015 inches to optimize the cutting effect.

The general characteristics of the jaw members 110 and 120 and the electrode assembly 105 will initially be described with respect to FIG. 3A while the changes to the other envisioned embodiments disclosed herein will become apparent during the description of each individual embodiment. Moreover, all of the following figures show the various electrical configurations and polarities during the cutting phase only. During the so called "sealing phase", the jaw members 110 and 120 are closed about tissue and the cutting elements 127 and 127b forms the requisite gap between the opposing sealing surfaces 112a, 122a and 112b, 122b. During activation of the sealing phase, the cutting elements 127a and 127b are not necessarily energized such that the majority of the current is concentrated between opposing sealing surfaces, 112a and 122a and 112b and 122b to effectively seal the tissue. It is also envisioned that stop members 1160a and 1160b may be employed to regulate the gap distance between the sealing surfaces in lieu of the cutting elements 127a and 127b. The stop members 1160a and 1160b may be disposed on the sealing surfaces 1112a, 1122a and 1112b, 1122b (See FIG. 4E), adjacent the sealing surfaces 1112a, 1122a and 1112b, 1122b or on the insulator(s) 1113, 1123.

The cutting elements 127a and 127b are preferably configured to extend from their respective insulators 113 and 123, respectively and extend beyond the tissue contacting surfaces 112a, 112b and 122a and 122b such that the cutting elements 127a and 127b act as stop members (i.e., creates a gap distance "G" (See FIG. 3A) between opposing conductive sealing surfaces 112a, 122a and 112b, 122b) which as mentioned above promotes accurate, consistent and effective tissue sealing. As can be appreciated, the cutting elements 127a and 127b also prevent the opposing tissue contacting surfaces 112a, 122a and 112b, 122b from touching which eliminates the chances of the forceps 10, 100 shorting during the sealing process.

As mentioned above, two mechanical factors play an important role in determining the resulting thickness of the sealed tissue and effectiveness of a tissue seal, i.e., the pressure applied between opposing jaw members 110 and 120 and the gap distance "G" between the opposing tissue contacting surfaces 112a, 122a and 112b, 122b during the sealing process. Preferably and with particular respect to vessels, the cutting element 127 (or cutting elements 127a and 127b) extends beyond the tissue contacting surfaces 112a, 112b and/or 122a, 122b to yield a consistent and accurate gap distance "G" during sealing within the range of about 0.001 inches to about 0.006 inches and, more preferably, within the range of about 0.002 inches and about 0.003 inches. Other gap ranges may be preferable with other tissue types such as bowel or large vascular structures. As can be appreciated, when utilizing one cutting element (as with some of the disclosed embodiments herein), e.g., 127, the cutting element 127 would be configured to extend beyond the sealing surfaces 112a, 112b and 122a, 122b to yield a gap distance within the above working range. When two opposing cutting elements are utilized, e.g., 127a and 127b, the combination of these cutting elements 127a and 127b yield a gap distance within the above working range during the sealing process.

With respect to FIG. 3A, the conductive cutting elements 127a and 127b are oriented in opposing, vertical registration within respective insulators 113 and 123 of jaw members 110 and 120. It is envisioned that the cutting elements 127a and 127b are substantially dull which, as can be appreciated, does not inhibit the sealing process (i.e., premature cutting) during the sealing phase of the electrosurgical activation. In other words, the surgeon is free to manipulate, grasp and clamp the tissue for sealing purposes without the cutting elements 127a and 127b mechanically cutting into the tissue. Moreover in this instance, tissue cutting can only be achieved through either: 1) a combination of mechanically clamping the tissue between the cutting elements 127a and 127b and applying electrosurgical energy from the cutting elements 127a and 127b, through the tissue and to the return electrodes, i.e., the electrically conductive tissue contacting surfaces 112b and 122b as shown in FIG. 3A; or 2) applying electrosurgical energy from the cutting elements 127a and 127b through the tissue and to the return tissue contacting surfaces 112b and 122b.

It is envisioned that the geometrical configuration of the cutting elements 127a and 127b play an important role in determining the overall effectiveness of the tissue cut. For example, the power density and/or current concentration around the cutting elements 127a and 127b is based upon the particular geometrical configuration of the cutting elements 127a and 127b and the cutting elements' 127a and 127b proximity to the return electrodes, i.e., tissue contacting surfaces 112b and 122b. Certain geometries of the cutting elements 127a and 127b may create higher areas of power density than other geometries. Moreover, the spacing of the return electrodes 112b and 122b to these current concentrations effects the electrical fields through the tissue. Therefore, by configuring the cutting elements 127a and 127b and the respective insulators 113 and 123 within close proximity to one another, the electrical power density remains high which is ideal for cutting and the instrument will not short due to accidental contact between conductive surfaces. As can be appreciated, the relative size of the cutting elements 127a and 127b and/or the size of the insulator 113 and 123 may be selectively altered depending upon a particular or desired purpose to produce a particular surgical effect.

In addition, the cutting element 127a (and/or 127b) may be independently activated by the surgeon or automatically activated by the Generator once sealing is complete. A safety algorithm may be employed to assure that an accurate and complete tissue seal is formed before cutting. An audible or visual indicator (not shown) may be employed to assure the surgeon that an accurate seal has been formed and the surgeon may be required to activate a trigger (or deactivate a safety) before cutting. For example, a smart sensor or feedback algorithm 1999 (See FIG. 5) may be employed to determine seal quality prior to cutting. The smart sensor or feedback loop 1999 may also be configured to automatically switch electrosurgical energy to the cutting element 127a (and/or 127b) once the smart sensor 1999 determines that the tissue is properly sealed. It is also envisioned that the electrical configuration of the electrically conductive sealing surfaces 112a, 112b and 122a, 122b may be automatically or manually altered during the sealing and cutting processes to effect accurate and consistent tissue sealing and cutting.

Turning now to the embodiments of the electrode assembly 105 as disclosed herein which show the various polarities during the tissue cutting phase, FIG. 3A as mentioned above includes first and second jaw members 110 and 120 having an electrode assembly 105 disposed thereon. More particularly, the electrode assembly 105 includes first electrically conductive sealing surfaces 112a and 112b each disposed in opposing registration with second electrically conductive sealing surfaces 122a and 122b on jaw members 110 and 120, respectively. Insulator 113 electrically isolates sealing surfaces 112a and 112b from one another allowing selective independent activation of the sealing surfaces 112a and 112b. Insulator 123 separates sealing surfaces 122a and 122b from one another in a similar manner thereby allowing selective activation of sealing surfaces 122a and 122b.

Preferably each insulator 113 and 123 is set back a predetermined distance between the sealing surfaces 112a, 112b and 122a, 122b to define a recess 149a, 149b and 159a, 159b, respectively, which, as mentioned above, effects the overall power densities between the electrically activated surfaces during both the sealing and cutting phases. Cutting element 127a is disposed within and/or deposited on insulator 113 and extends inwardly therefrom to extend beyond the sealing surfaces 112a, 112b by a predetermined distance. In the embodiments wherein only one cutting element, e.g., 127a is shown, the cutting element 127a extends beyond the sealing surfaces 112a, 112b and 122a and 122b to define the aforementioned gap range between the opposing sealing surfaces 112a, 122a and 112b and 122b. When two (or more) cutting elements 127a and 127b are employed (i.e., at least one disposed within each insulator 113 and 123) the combination of the cutting elements 127a and 127b yield the desired gap distance within the working gap range.

During sealing, the opposing sealing surfaces 112a, 122a and 112b, 122b are activated to seal the tissue disposed therebetween to create two tissue seals on either side of the insulators 113 and 123. During the cutting phase, the cutting elements 127a and 127b are energized with a first electrical potential "+" and the right opposing sealing surfaces 112b and 122b are energized with a second electrical potential "−". This creates a concentrated electrical path between the potentials "+" and "−" through the tissue to cut the tissue between the previously formed tissue seals. Once the tissue is cut, the jaw members 110 and 120 are opened to release the two tissue halves.

FIG. 3B discloses another embodiment according to the present disclosure which includes similar elements as described above with respect to FIG. 3A, namely, sealing surfaces 312a, 312b and 322a, 322b, insulators 313 and 323 and cutting elements 327a and 327b with the exception that the left side of each insulator 313 and 323 is extended beyond sealing surfaces 312a and 322a to a position which is flush with the cutting elements 327a and 327b. The right side of each insulator 313 and 323 is set back from sealing surfaces 312a and 312b, respectively. It is envisioned that configuring the electrode assembly 305 in this fashion will reduce stray current concentrations between electrically conductive surfaces 312a, 312b and 322a, 322b and cutting elements 327a and 327b especially during the cutting phase.

FIG. 3C discloses yet another embodiment according to the present disclosure and includes similar elements as above, namely, sealing surfaces 412a, 412b and 422a, 422b, insulators 413 and 423 and cutting elements 327a and 327b. With this particular embodiment, during the cutting phase, both sets of opposing sealing surfaces 412a, 422a and 412b, 422b are energized with the second electrical potential "−" and the cutting elements 427a and 427b are energized to the first electrical potential "+". It is believed that this electrode assembly 405 will create concentrated electrical paths between the potentials "+" and "−" through the tissue to cut the tissue between the previously formed tissue seals.

FIG. 3D shows an electrode assembly 505 configuration similar to FIG. 3B with a similar electrical configuration to the embodiment of FIG. 3C. The electrode assembly 505 includes and includes similar components as described above, namely, sealing surfaces 512a, 512b and 522a, 522b, insulators 513 and 523 and cutting elements 527a and 527b. The opposing sealing electrodes 512a, 522b and 512a, 522b are energized to the second electrical potential "−" during the cutting phase, which as described above is believed to enhance tissue cutting. It is envisioned that with particular embodiments like FIGS. 3C and 3D, it may be easier to manufacture the electrode assembly 505 such that all of the sealing surfaces 512a, 512b and 522a, 522b are energized to the same electrical potential rather than employ complicated switching algorithms and/or circuitry to energize only select sealing surfaces like FIGS. 3A and 3B.

FIG. 3E shows yet another embodiment of the electrode assembly 605 which includes opposing sealing surfaces 612a, 622a and 612b, 622b, cutting element 627 and insulators 613 and 623. As can be appreciated by this particular embodiment, the electrode assembly 605 only includes one cutting element 627 disposed within insulator 613 for cutting tissue. The cutting element 627 is disposed opposite insulator 623 which provides a dual function during activation of the electrode assembly 605: 1) provides a uniform gap between sealing surfaces 612a, 622a and 612b, 622b during the sealing phase; and 2) prevents the electrode assembly 605 from shorting during the sealing and cutting phases. During activation, the cutting element 627 is energized to a first potential "+" and the opposing sealing surfaces 612a, 622a and 612b, 622b are energized to a second electrical potential "−" which creates an area of high power density between the two previously formed tissue seals and cuts the tissue.

FIG. 3F shows yet another alternate embodiment of the electrode assembly 705 which includes similar elements as described above, namely, sealing surfaces 712a, 712b and 722a, 722b, cutting elements 727a and 727b and insulators 713 and 723. During activation, only three of the four sealing surfaces are energized to the second potential "−", e.g., sealing surfaces 712a, 712b and 722b while the cutting elements 727a and 727b are energized to the first potential "+". It is envisioned that during the cutting phase, this particular electrode assembly 705 arrangement will produce a diagonally-oriented, left-to-right cut line between the previously formed tissue seals which may be suited for a particular surgical purpose.

FIGS. 4A and 4B shows yet another embodiment of the electrode assembly 805 according to the present disclosure showing tissue disposed between the two jaw members 810 and 820 prior to activation of the sealing surfaces 812a, 812b and 822a, 822b. With this particular embodiment, the insulators 813 and 823 are configured to have opposing triangular like cross sections which essentially "pinch" the tissue between the insulators 813 and 823 when tissue is grasped between jaw members 810 and 820. During sealing, energy is applied to the tissue through the opposing sealing plates 812a, 822a and 812b, 822b to effect two tissue seals on either side of the insulators 813 and 823. During the cutting phase, sealing electrodes 812a and 822a are energized to a first potential "+" and sealing plates 812b and 822b are energized to the second electrical potential "−" such that energy flows in the direction of the indicated arrow "A". In other words, it is believed that the pinching of the tissue tends to control or direct the energy concentration to specific tissue areas to effect tissue cutting.

Turning now to FIGS. 4C-4J which show various geometrical configurations for the upper jaw member 910 for the electrode assembly 905 which may be utilized with a symmetrical or asymmetrical lower jaw member (not shown) to effectively seal and subsequently cut tissue. Using the various geometries of the jaw members tends to "pinch" the tissue during sealing prior to separation which is envisioned will enhance the tissue cutting process especially when the pinched tissue areas are subject to high power densities. For the purposes herein, the pinch may be described as the area of smallest tissue volume anywhere between the active tissue poles. Typically, the pinched tissue area is associated with high pressure. Many of the below described jaw configurations illustrate the pinch concept and are envisioned to utilize a variety of polarity configurations to enhance or facilitate cutting. For the purposes of clarification, only the polarity associated with the cutting phase is depicted on each figure.

Moreover, it is envisioned that any combination of electrical potential as hereinbefore described may be utilized with the various jaw members (and each jaw member's opposing jaw member) to effectively seal tissue during a first electrical phase and cut tissue during a subsequent electrical phase. As such, the illustrated jaw members are labeled with a first electrical potential "+", however, it is envisioned that the lower jaw member inclusive of the sealing surfaces and cutting elements (which may or may not be a mirror image of the upper jaw member) may be energized with any combination of first and second electrical potential(s) (or other electrical potentials) to effectively seal and subsequently cut tissue disposed between the jaw members.

FIG. 4C shows one particular upper jaw member 910 which includes a sealing surface 912 having a U-shaped recess 921 defined therein for housing insulator 913. A cutting element 927 is disposed within insulator 913 and is dimensioned to extend beyond the sealing surface 912. The cutting element 927 may be an electrode or may be made from a partially conductive material. FIG. 4D shows a jaw member 1010 which forms part of an electrode assembly 1005 which includes two sealing surfaces 1012a and 1012b with an insulator 1013 disposed therebetween. The insulator 1013 includes a cutting element 1027 disposed therein which extends beyond the sealing surfaces 1012a and 1012b much like the embodiments described above with respect to FIGS. 3A-3F. Again the cutting element 1027 may be an electrode or made from a semi-conductor material. However and as mentioned above, a different geometrically-shaped jaw member may be disposed opposite jaw member 1010 with different electrical potentials to produce a particular sealing and cutting effect.

FIGS. 4E-4J show various geometrical configurations of at least one jaw member which is configured to both seal tissue during a first sealing phase and cut tissue during a subsequent cutting phase. In each instance, the particular geometrical configuration of the insulator is designed to focus current into high areas of power density to produce a cutting effect and/or reduce the likelihood of current straying to adjacent tissue which may ultimately damage the adjacent tissue structures.

For example, FIG. 4E shows a jaw member 1110 which may be utilized with the electrode assembly 1105 which includes sealing surfaces 1112a and 1112b which are separated by a partially conductive material 1113. A mirror-like jaw member 1120 is shown in opposition to jaw member 1110 and includes similar elements, namely, sealing surfaces 1122a and 1122b and partially conductive material 1123. In this particular embodiment, the partially conductive materials 1113 and 1123 are generally rounded to include and apexes 1151a and 1151b, respectively, which extend beyond the sealing surfaces 1112a, 1112b and 1122a, 1122b. The partially conductive materials 1113 and 1123 are preferably made from a material which have conductive properties which over time generate areas of high power density at the apexes 1151a and 1151b to cut tissue disposed thereunder. A series of stop members 1160a and 1160 and preferably disposed on surfaces 1112a and 1122b and prevent the apexes 1151a and 1151b from touching and shorting.

It is envisioned that during the sealing phase (not shown) the partially conductive materials 1113 and 1123 are not energized and will generally act more as insulating materials since by its nature it is only semi-conductive and are not as conductive as sealing surfaces 1112a, 1112b and 1122a, 1122b. In other words, the current will be supplied to the sealing plates 1112a, 1112b and 1122a, 1122b and not directly to the partially conductive materials 1113 and 1123 thereby producing the majority of the electrical effect between the opposing sealing plates 1112a, 1122a and 1112b, 1122b of the jaw members 1110 and 1120. During the cutting phase (as shown), an electrical potential is supplied directly to the partially conductive materials 1113 and 1123 which is believed will make them more conductive and which produce areas of high power density in the vicinity of the apexes 1151a and 1151b to cut the tissue.

For example, partially conductive material 1113 is supplied with a first potential and partially conductive material 1123 is supplied with a second potential to facilitate cutting. Jaw member 1120 may also be configured to include a different geometrical configuration from jaw member 1110 to produce a particular cutting effect. Moreover, an insulator (not shown) may be disposed between one or both of the partially conductive materials 1113 and 1123 and its respective sealing surface to reduce electrical conduction or heat transfer between or across these elements.

FIG. 4F shows a similar electrode assembly 1205 having sealing surfaces 1212a and 1212b which are separated by a partially conductive material 1213 and wherein the partially conductive material 1213 is generally rounded but does not extend beyond the sealing surfaces 1212a and 1212b. The partially conductive material 1213 is preferably made from a material such as those identified above which produces an area of high power density at the apex 1251 to cut tissue disposed thereunder during the cutting phase. Again, the opposite jaw member (not shown) may be configured as a mirror image of the jaw member 1210 or may include a different geometrical configuration.

FIG. 4G shows another geometric configuration of a jaw member 1310 which includes sealing surfaces 1312a and 1312b separated by a partially conductive material 1313 wherein the partially conductive material is set back between the sealing surface 1312a and 1312b to define a recess 1349 therein. FIG. 4H shows yet another geometric configuration of a jaw member 1410 which forms part of an electrode assembly 1405 and which includes sealing surface 1412 and a partially conductive material 1413. As can be appreciated this particular arrangement does not include a second sealing surface on the upper jaw member 1410 but instead the partially conductive material 1413 includes a notch-like recess 1449 defined therein which has a cutting tip 1451 which extends beyond sealing surface 1412. It is envisioned that the cutting tip 1451 extends beyond the sealing surface 1412 enough to both maintain the necessary gap distance during the sealing phase and to eventually facilitate tissue cutting during the cutting phase by producing an area of high power density at the tip 1451. Again, the opposite jaw member (not shown) may be configured as a mirror image of the jaw member 1410 or may include a different geometrical configuration.

Figure 4I:
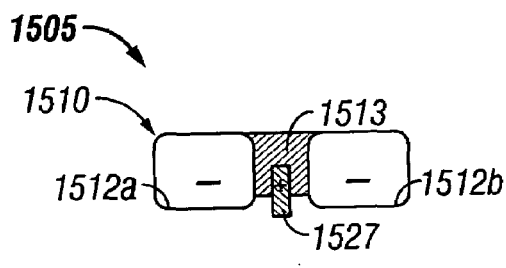

FIG. 4I includes yet another geometric configuration of the upper jaw member 1510 which forms part of an electrode assembly 1505 and which includes sealing surfaces 1512a and 1512b which are separated by an insulator 1513. The insulator 1513 includes a generally rectilinear-shaped semi-conductive cutting element 1527 disposed therein which extends beyond the sealing surfaces 1512a and 1512b. As can be appreciated, during the cutting phase, the semi-conductive cutting element 1527 is energized by a first potential "+" and the sealing plates 1512a, 1512b is energized to a second potential "−". The insulator 1513 isolates the potentials between the partially conductive material 1527 and the sealing surfaces 1512a and 1512b during activation.

Figure 4J:
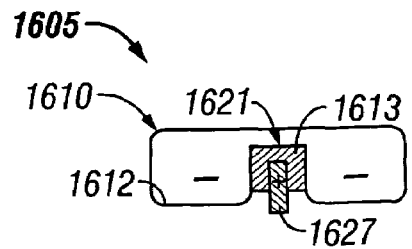

FIG. 4J shows still yet another geometric configuration showing a jaw member 1610 for an electrode assembly 1605 which is similar to FIG. 4C above which includes a C-shaped sealing plate 1612 having a recess 1621 defined therein for housing an insulator 1613. The insulator 1613 includes a semi-conductive cutting element 1627 housed therein for cutting tissue. During the cutting phase, the semi-conductive cutting element 1627 is energized to a first potential "+" and the sealing plate 1612 is energized to a second potential "−" to effect tissue cutting. Again, the lower or second jaw member (not shown) may include the same geometric configuration to enhance the cutting process.

Figure 5:
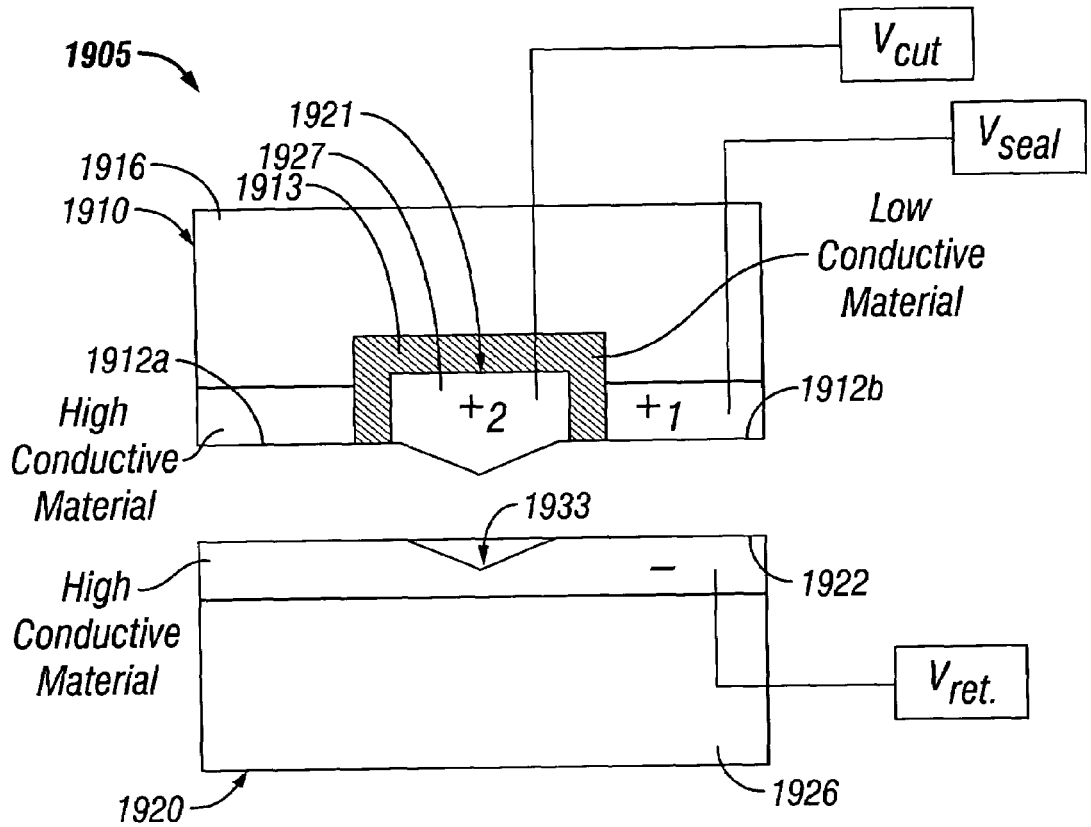
FIG. 5 is a schematic end view showing an alternate configuration of an electrode assembly according to the present invention with the electrical potentials for both the sealing phase and the cutting phase identified.

FIG. 5 shows a schematically-illustrated example of electrical circuitry for an electrode assembly 1905 which may be utilized to initially seal tissue between the sealing plates and subsequently cut tissue once the tissue seal(s) are formed. More particularly, jaw member 1910 includes insulative housing 1916 which is dimensioned to house conductive sealing plates 1912a and 1912b with an insulator or partially conductive material 1913 disposed therebetween. Insulator/partially conductive material 1913 includes a recess 1921 defined therein which is dimensioned to retain a generally triangularly-shaped cutting element 1927 which extends beyond sealing surfaces 1912a and 1912b. Jaw member 1920 includes an outer insulative housing 1926 which is dimensioned to house electrically conductive sealing surface 1922. Sealing surface 1922 includes a recess 1933 defined therein which generally compliments the cross sectional profile of cutting element 1927. Preferably, the cutting element 1927 is dimensioned slightly larger than the recess 1933 such that a gap is formed when the jaw members are closed about tissue, the gap being within the above-identified working range.

During sealing (Vseal), the sealing plates 1912a and 1912b are energized to a first potential "+$_1$" and sealing plate 1922 is energized to a second potential "−". The cutting element is not energized. Since the insulator or semi-conductor does not conduct energy as well as the conductive sealing plates 1912a and 1912b, the first potential is not effectively or efficiently transferred to the cutting element 1927 and the tissue is not necessarily heated or damaged during the sealing phase. During the sealing phase energy is transferred from the sealing plates 1912a and 1912b through the tissue and to the return electrode 1922 (Vreturn). It is believed that even if some energy is effectively transferred to the cutting element 1927 during the sealing phase, it will simply preheat or pre-treat the tissue prior to separation and should not effect the cutting phase. During the sealing phase, the cutting element 1927 mainly acts as a stop member for creating and maintaining a gap between the opposing sealing surfaces 1912a, 1912b and 1922.

During the cutting phase (Vcut), a first potential "+$_2$" is supplied to the cutting element 1927 and a second potential "−" is supplied to the sealing surface 1922. The electrical parameters (power, current, waveform, etc.) associated with this phase may be the same or different than the potentials used for the sealing phase. It is believed that similar first and second potentials may be utilized since different components with varying geometries are being energized which by themselves are envisioned to create different electrical effects. As can be appreciated, during the cutting phase energy is transferred from the cutting element 1927 through the tissue and to the return electrode 1922 (Vreturn). It is believed that even if some energy is transferred to the sealing plates 1912a and 1912b during the cutting phase through the insulator/semi-conductor 1913, it will not detrimentally effect the already formed tissue seals. Moreover, it is believed that one or more sensors (not shown), computer algorithms and/or feedback controls associated with the generator or internally disposed within the forceps may be employed to prevent overheating of the tissue during the sealing and cutting phases.

Figure 6A:
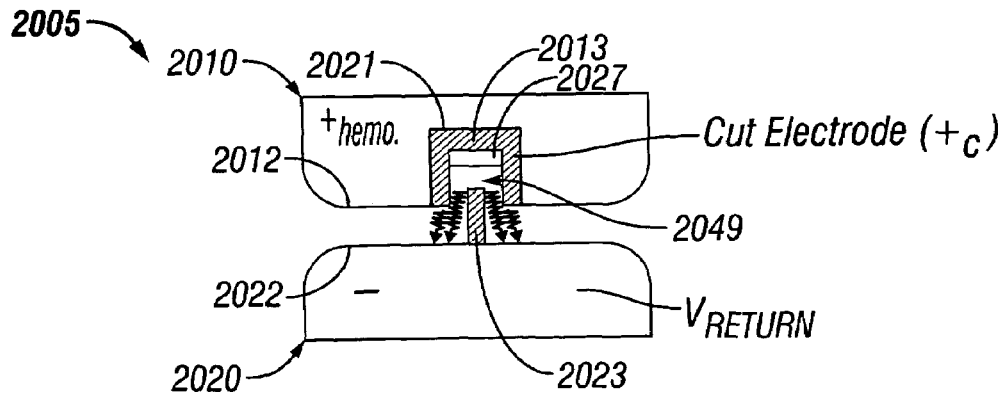
FIGS. 6A-6D are enlarged, schematic end views showing alternate configurations of the electrode assembly according to the present invention with the electrical potentials for both the sealing mode and the cutting mode identified.

FIGS. 6A-6D show additional embodiments of jaw members having various electrode assemblies which may be utilized for sealing and cutting tissue disposed between the jaw members. For example, FIG. 6A shows a first or upper jaw member 2010 for use with an electrode assembly 2005 which includes an electrically conductive sealing surface 2012 having a recess 2021 defined therein dimensioned to house an insulator 2013. The insulator also includes a notch 2049 disposed therein which partially houses a generally rectilinearly-shaped cutting electrode 2027. Electrode 2027 is preferably recessed or set back within notch 2049. Jaw member 2020 includes an electrically conductive sealing surface 2022 which is disposed in substantial vertical registration with opposing sealing surface 2012. Sealing surface 2022 includes a generally rectilinearly-shaped insulator 2023 which extends towards jaw member 2010 and is configured to abut electrode 2027 when the jaw members 2010 and 2020 are moved into the closed position about tissue. As can be appreciated, the insulator 2023 acts as a stop member and creates a gap distance within the above working range during the sealing process. In addition, the two insulators 2013 and 2023 insulate the upper jaw member 2010 during the cutting phase and generally direct the cutting current from the cutting element 2027 in an intense fashion towards the return electrode 2022 (Vreturn) to effectively cut tissue.

Figure 6B:
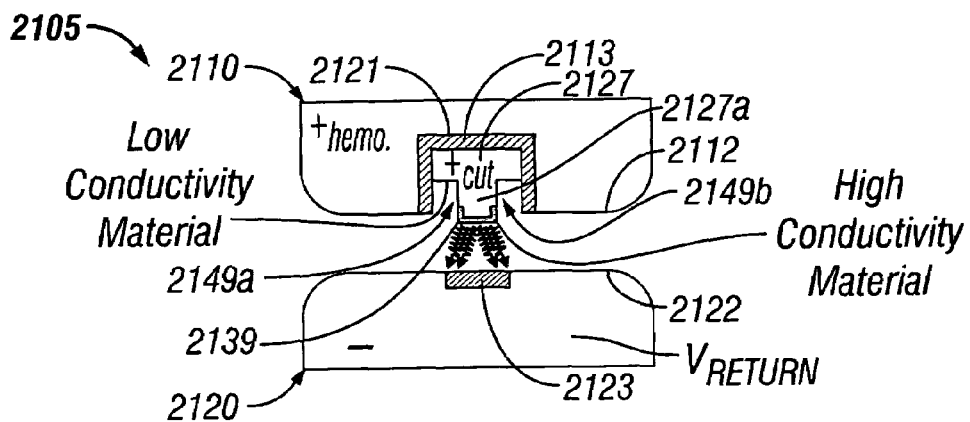

FIG. 6B shows yet another embodiment of an electrode assembly 2105 disposed on jaw members 2110 and 2120. More particularly, jaw members 2110 and 2120 include electrically conductive sealing surfaces 2112 and 2122, respectively, disposed in general vertical registration relative to one another and which are configured to seal tissue during the sealing phase. Much like the embodiment described above with respect to FIG. 6A, jaw member 2110 includes a recess 2121 defined therein dimensioned to house an insulator 2113. Jaw member 2120 includes an electrically conductive sealing surface 2122 which is disposed in substantial vertical registration with opposing sealing surface 2112. Jaw member 2120 includes an insulator 2123 disposed therein which is disposed opposite recess 2121.

The insulator 2113 also includes a T-shaped cutting element 2127 housed therein which defines two notches 2149a and 2149b on either side of a leg or extension 2127a which extends towards jaw member 2120. The cutting element 2127 is preferably made from a relatively low conductive material and includes an area of highly conductive material 2139 disposed at the distal end of the leg 2127a. The highly conductive material 2139 is disposed in vertical registration with the insulator 2123 disposed in jaw member 2120. During activation of the cutting phase, it is believed that the highly conductive material 2139 will focus the cutting current in an intense fashion towards the return electrode 2122 (Vreturn) to cut the tissue disposed between jaw members 2110 and 2120.

Figure 6C:
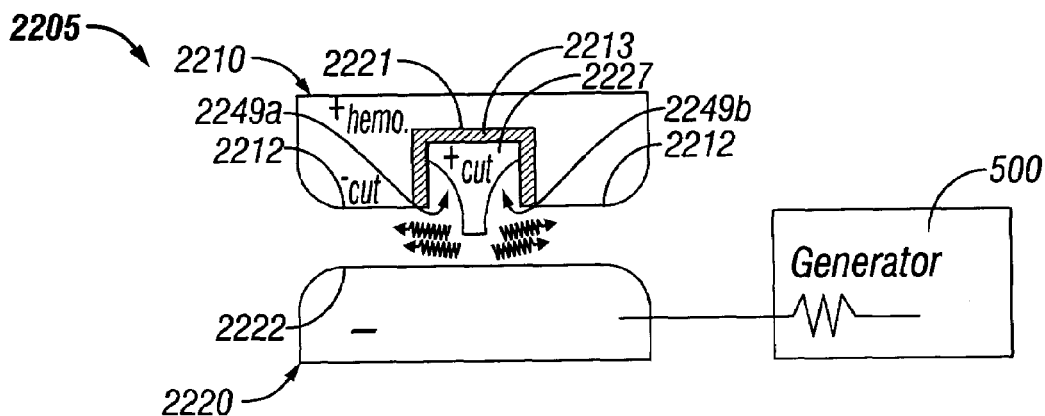

FIG. 6C shows yet another set of jaw members 2210 and 2220 with an electrode assembly 2205 disposed thereon for sealing and cutting tissue. More particularly, jaw member 2210 includes an electrically conductive sealing surface 2212 having a recessed portion 2221 disposed therein for housing an insulator 2213 which, in turn, houses a generally V-shaped cutting element 2227 therein. Jaw member 2220 includes an electrically conductive sealing surface 2222 which opposes sealing surface 2212 on jaw member 2210. During the sealing phase, sealing surfaces 2212 and 2222 conduct electrosurgical energy through tissue held therebetween to effect a tissue seal. V-shaped cutting element 2227 acts as a stop member during the sealing phase.

During the cutting phase, V-shaped cutting element 2227 pinches the tissue held between the jaw members 2210 and 2220 and when activated directs electrosurgical energy through the tissue in an intense fashion around insulator 2213 and towards sealing surface 2212. Jaw member 2220 remains neutral during the cutting phase and is not believed to significantly alter the direction of the electrical path to adversely effect the cutting process.

Figure 6D:
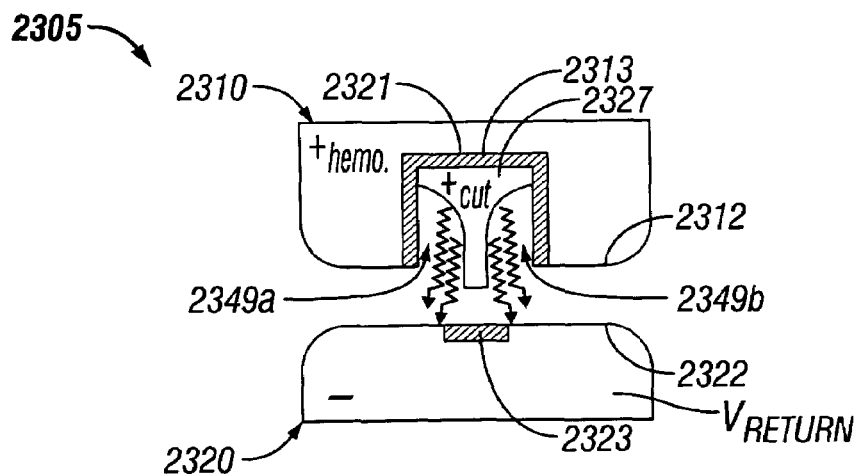

FIG. 6D shows yet another embodiment of jaw members 2310 and 2320 having an alternative electrode assembly 2305 for sealing and cutting tissue. More particularly, the electrode assembly 2305 is similar to the electrode configuration of the embodiment described with respect to FIG. 6C with the exception that the lower jaw member 2320 includes an insulator 2323 disposed in vertical registration with the cutting element 2327 disposed within the recess 2321 of the upper jaw member 2310. In this instance, the cutting element 2327 is dimensioned to be wider than the insulator 2323 such that the rear portions of the V-shaped cutting element extend laterally beyond the insulator 2323 when the jaw members 2310 and 2320 are disposed in the closed position. In other words, the cutting element 2327 includes an overhang portion which is disposed in opposing vertical registration with the return electrode 2322. The insulator 2313 disposed within the recess 2321 of the upper jaw member 2310 helps to direct the electrosurgical energy towards the return electrode 2322 during cuffing and reduces stray currents to adjacent tissue structures.

During the sealing phase, sealing surfaces 2312 and 2322 conduct electrosurgical energy through tissue held therebetween to effect two tissues seals on opposite sides of insulator 2313. V-shaped cutting element 2327 acts as a stop member during the sealing phase. During the cutting phase, jaw member 2310 is neutralized and cutting element 2327 is energized such that electrosurgical energy is directed from the cutting element 2327 through tissue held between the jaw members 2310 and 2320 and to the return electrode 2322 (Vreturn). It is believed that the V-shaped cutting element 2327 will direct energy to the return electrode 2322 in an intense fashion around insulator 2323 and towards sealing surface 2212 to effectively cut the tissue between the already formed tissue seals.

Figure 7A:
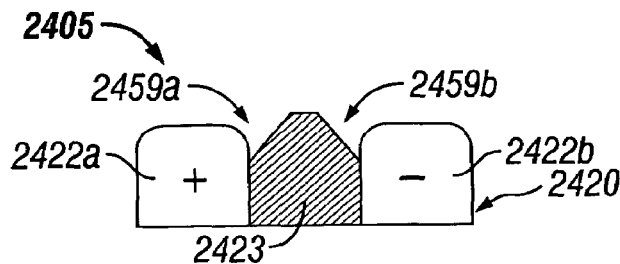
FIGS. 7A-7E are enlarged, schematic end views showing various configurations for the lower jaw member to promote electrical cutting.

FIGS. 7A-7D show various geometric configurations of cutting elements and insulators for use with the electrode assemblies of forceps 10, 100 according to the present disclosure. For example, FIG. 7A shows one embodiment wherein one of the electrode assemblies 2405 includes jaw members 2420 having first and second electrically conductive sealing surfaces 2422a and 2422b which are of opposite electrical potentials and which are separated by a trapeziodally-shaped insulator 2423 which extends beyond each respective sealing surface 2422a and 2422b. As can be appreciated the particular shape of the frustoconically-shaped insulator 2423 forms two recessed portions 2459a and 2459b between the sealing surfaces 2422a, 2422b and the insulator 2423 which is envisioned to both pinch the tissue between the insulator 2423 and the opposing surface (e.g., another insulator or conductive surface) and control the electrosurgical energy during activation to facilitate cutting.

Figure 7B:
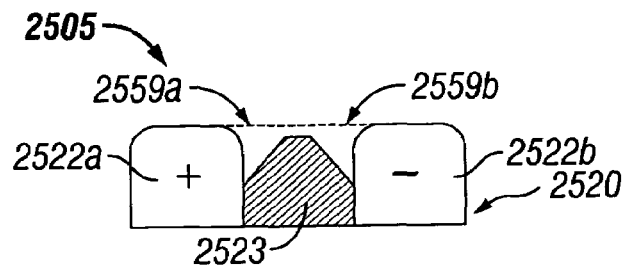

FIG. 7B shows another similar embodiment which includes a frustoconically-shaped insulator 2523 which does not extend beyond the sealing surfaces 2522a and 2522b but is actually slightly set back from the sealing surfaces 2522a and 2522b. Again, the particular shape of the trapeziodally-shaped insulator 2523 forms two recessed portions 2559a and 2559b between the sealing surfaces 2522a, 2522b and the insulator 2523 which is envisioned to control the electrosurgical energy during activation to enhance the cutting process.

Figure 7C:
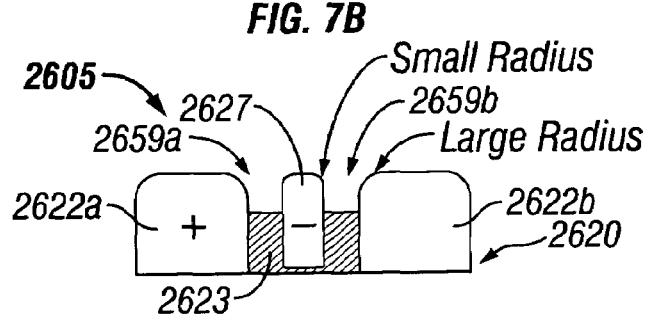

FIG. 7C shows another geometrical configuration of an electrode assembly 2605 which includes one active electrically conductive surface 2622a and one neutral electrically conductive surface 2622b during the cutting phase. A cutting element 2627 is disposed between the two surfaces 2622a and 2622b and is separated from the surfaces by an insulator 2623 which is recessed between the two surfaces 2622a and 2622b to form notches or set back areas 2659a and 2659b. The cutting element 2627 is designed with a smaller radius of curvature than the active electrode 2622a such that during the cutting phase, electrosurgical energy is intensified to create a sufficient power density to effectively cut tissue proximate the cutting element 2627.

Figure 7D:
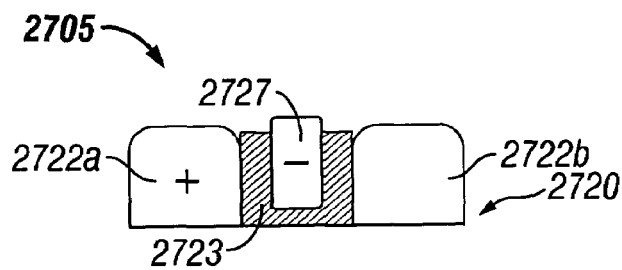

FIG. 7D shows another geometric configuration of an electrode assembly 2705 similar to the embodiment shown in FIG. 7C above wherein the insulator 2723 is configured to be generally flush with the surfaces 2722a and 2722b. The cutting element 2727 is disposed within the insulator 2723 and extends from both the insulator 2723 and the surfaces 2722a and 2722b towards an opposing surface on the other jaw member (not shown). It is believed that the shape of the insulator 2723 will direct intensified electrosurgical current between the cutting element 2727 and the active conductive surface 2722a.

Figure 7E:
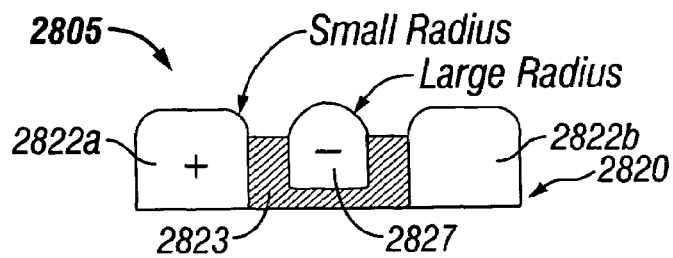

FIG. 7E shows yet another electrode assembly 2805 having a jaw member 2820 with a geometric configuration similar FIG. 7C above wherein the insulator 2823 is recessed between the two sealing surfaces 2822a and 2822b. A generally rounded cutting element 2827 is disposed within the insulator 2823. The cutting element 2827 includes a larger radius of curvature than the radius of curvature of the active surface 2822a such that during the cutting phase, electrosurgical energy is intensified to effectively cut tissue proximate the cutting element 2827.

As can be appreciated, the various geometrical configurations and electrical arrangements of the aforementioned electrode assemblies allow the surgeon to initially activate the two opposing electrically conductive tissue contacting surfaces and seal the tissue and, subsequently, selectively and independently activate the cutting element and one or more tissue contacting surfaces to cut the tissue utilizing the various above-described and shown electrode assembly configurations. Hence, the tissue is initially sealed and thereafter cut without re-grasping the tissue.

However, it is envisioned that the cutting element and one or more tissue contacting surfaces may also be activated to simply cut tissue/vessels without initially sealing. For example, the jaw members may be positioned about tissue and the cutting element may be selectively activated to separate or simply coagulate tissue. This type of alternative embodiment may be particularly useful during certain endoscopic procedures wherein an electrosurgical pencil is typically introduced to coagulate and/or dissect tissue during the operating procedure.

A switch 70 may be employed to allow the surgeon to selectively activate one or more tissue contacting surfaces or the cutting element independently of one another. As can be appreciated, this allows the surgeon to initially seal tissue and then activate the cutting element by simply turning the switch. Rocker switches, toggle switches, flip switches, dials, etc. are types of switches which can be commonly employed to accomplish this purpose. It is also envisioned that the switch may cooperate with the smart sensor (or smart circuit, computer, feedback loop, etc.) which automatically triggers the switch to change between the "sealing" mode and the "cutting" mode upon the satisfaction of a particular parameter. For example, the smart sensor may include a feedback loop which indicates when a tissue seal is complete based upon one or more of the following parameters: tissue temperature, tissue impedance at the seal, change in impedance of the tissue over time and/or changes in the power or current applied to the tissue over time. An audible or visual feedback monitor may be employed to convey information to the surgeon regarding the overall seal quality or the completion of an effective tissue seal. A separate lead may be connected between the smart sensor and the generator for visual and/or audible feedback purposes.

Preferably, the generator 500 delivers energy to the tissue in a pulse-like waveform. It has been determined that delivering the energy in pulses increases the amount of sealing energy which can be effectively delivered to the tissue and reduces unwanted tissue effects such as charring. Moreover, the feedback loop of the smart sensor can be configured to automatically measure various tissue parameters during sealing (i.e., tissue temperature, tissue impedance, current through the tissue) and automatically adjust the energy intensity and number of pulses as needed to reduce various tissue effects such as charring and thermal spread.

It has also been determined that RF pulsing may be used to more effectively cut tissue. For example, an initial pulse from the cutting element through the tissue (or the tissue contacting surfaces through the tissue) may be delivered to provide feedback to the smart sensor for selection of the ideal number of subsequent pulses and subsequent pulse intensity to effectively and consistently cut the amount or type of tissue with minimal effect on the tissue seal. If the energy is not pulsed, the tissue may not initially cut but desiccate since tissue impedance remains high during the initial stages of cutting. By providing the energy in short, high energy pulses, it has been found that the tissue is more likely to cut.

Alternatively, a switch may be configured to activate based upon a desired cutting parameter and/or after an effective seal is created or has been verified. For example, after effectively sealing the tissue, the cutting element may be automatically activated based upon a desired end tissue thickness at the seal.

As mentioned in many of the above embodiments, upon compression of the tissue, the cutting element acts as a stop member and creates a gap "G" between the opposing conductive tissue contacting surfaces. Preferably and particularly with respect to vessel sealing, the gap distance is in the range of about 0.001 to about 0.006 inches. As mentioned above, controlling both the gap distance "G" and clamping pressure between conductive surfaces are two important mechanical parameters which need to be properly controlled to assure a consistent and effective tissue seal. The surgeon activates the generator to transmit electrosurgical energy to the tissue contacting surfaces and through the tissue to effect a seal. As a result of the unique combination of the clamping pressure, gap distance "G" and electrosurgical energy, the tissue collagen melts into a fused mass with limited demarcation between opposing vessel walls.

Once sealed, the surgeon activates the cutting element to cut the tissue. As mentioned above, the surgeon does not necessarily need to re-grasp the tissue to cut, i.e., the cutting element is already positioned proximate the ideal, center cutting line of the seal. During the cutting phase, highly concentrated electrosurgical energy travels from the cutting element through the tissue to cut the tissue into two distinct halves. As mentioned above, the number of pulses required to effectively cut the tissue and the intensity of the cutting energy may be determined by measuring the seal thickness and/or tissue impedance and/or based upon an initial calibrating energy pulse which measures similar parameters. A smart sensor (not shown) or feedback loop may be employed for this purpose.

As can be appreciated, the forceps may be configured to automatically cut the tissue once sealed or the instrument may be configured to permit the surgeon to selectively divide the tissue once sealed. Moreover, it is envisioned that an audible or visual indicator (not shown) may be triggered by a sensor (not shown) to alert the surgeon when an effective seal has been created. The sensor may, for example, determine if a seal is complete by measuring one of tissue impedance, tissue opaqueness and/or tissue temperature. Commonly-owned U.S. application Ser. No. 10/427,832 which is hereby incorporated by reference herein describes several electrical systems which may be employed to provide positive feedback to the surgeon to determine tissue parameters during and after sealing and to determine the overall effectiveness of the tissue seal.

Preferably, the electrosurgical intensity from each of the electrically conductive surfaces and cutting elements is selectively or automatically controllable to assure consistent and accurate cutting along the centerline of the tissue in view of the inherent variations in tissue type and/or tissue thickness. Moreover, it is contemplated that the entire surgical process may be automatically controlled such that after the tissue is initially grasped the surgeon may simply activate the forceps to seal and subsequently cut tissue. In this instance, the generator may be configured to communicate with one or more sensors (not shown) to provide positive feedback to the generator during both the sealing and cutting processes to insure accurate and consistent sealing and division of tissue. As mentioned above, commonly-owned U.S. patent application Ser. No. 10/427,832 discloses a variety of feedback mechanisms which may be employed for this purpose.

From the foregoing and with reference to the various figure drawings, those skilled in the art will appreciate that certain modifications can also be made to the present disclosure without departing from the scope of the present disclosure. For example, it is contemplated that cutting element may be dimensioned as a cutting wire which is selectively activatable by the surgeon to divide the tissue after sealing. More particularly, a wire is mounted within the insulator between the jaw members and is selectively energizable upon activation of the switch.

The forceps may be designed such that it is fully or partially disposable depending upon a particular purpose or to achieve a particular result. For example, the electrode assembly may be selectively and releasably engageable with the distal end of the shaft and/or the proximal end of shaft may be selectively and releasably engageable with the housing and the handle assembly. In either of these two instances, the forceps would be considered "partially disposable" or "reposable", i.e., a new or different electrode assembly (or electrode assembly and shaft) selectively replaces the old electrode assembly as needed.

It is envisioned that the electrode assembly could be selectively detachable (i.e., reposable) from the shaft depending upon a particular purpose, e.g., it is contemplated that specific forceps could be configured for different tissue types or thicknesses. Moreover, it is envisioned that a reusable forceps could be sold as a kit having different electrodes assemblies for different tissue types. The surgeon simply selects the appropriate electrode assembly for a particular tissue type.

It is also envisioned that the forceps could include a mechanical or electrical lockout mechanism which prevents the sealing surfaces and/or the cutting element from being unintentionally activated when the jaw members are disposed in the open configuration.

Although the subject forceps and electrode assemblies have been described with respect to preferred embodiments, it will be readily apparent to those having ordinary skill in the art to which it appertains that changes and modifications may be made thereto without departing from the spirit or scope of the subject devices. For example, although the specification and drawing disclose that the electrically conductive surfaces may be employed to initially seal tissue prior to electrically cutting tissue in one of the many ways described herein, it is also envisioned that the electrically conductive surfaces may be configured and electrically designed to perform any known bipolar or monopolar function such as electrocautery, hemostasis, and/or desiccation utilizing one or both jaw members to treat the tissue. Moreover, the jaw members in their presently described and illustrated formation may be energized to simply cut tissue without initially sealing tissue which may prove beneficial during particular surgical procedures. Moreover, it is contemplated that the various geometries of the jaw members, cutting elements, insulators and semi-conductive materials and the various electrical configurations associated therewith may be utilized for other surgical instrumentation depending upon a particular purpose, e.g., cutting instruments, coagulation instruments, electrosurgical scissors, etc.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed:

1. An end effector assembly for use with an instrument for sealing and cutting vessels and/or tissue, the end effector assembly comprising:
   a pair of opposing first and second jaw members at least one of which being movable relative to the other from a first position wherein the jaw members are disposed in spaced relation relative to one another to a second position wherein the jaw members cooperate to grasp tissue therebetween;
   each jaw member including a pair of spaced apart, electrically conductive tissue sealing surfaces extending along a length thereof, each tissue sealing surface being adapted to connect to a source of electrosurgical energy such that the tissue sealing surfaces are capable of conducting electrosurgical energy through tissue held therebetween to effect a seal;
   an insulator disposed between each pair of electrically conductive sealing surfaces;
   the first jaw member including an electrically conductive cutting element disposed within the insulator of the first jaw member, the electrically conductive cutting element disposed in general vertical registration to the insulator on the second jaw member;
   wherein the cutting element extends from the first electrically conductive tissue sealing surface towards the second electrically conductive tissue sealing surface to create a gap between the electrically conductive tissue sealing surfaces when the jaw members close for sealing tissue;
   the cutting element being inactive during the sealing process and the pair of spaced apart electrically conductive sealing surfaces on the first jaw member being energized to a different potential from the corresponding pair of spaced apart electrically conductive sealing surfaces on the second jaw member such that electrosurgical energy can be transferred through the tissue to effect a tissue seal; and
   the cutting element being energized to a first potential during the cutting process and at least one electrically conductive tissue sealing surface on the first jaw member and at least one electrically conductive tissue sealing surface on the second jaw member being energized to a different potential such that electrosurgical energy can be transferred through the tissue to effect a tissue cut.

2. An end effector assembly according to claim 1 wherein the cutting and sealing processes are automatically controlled by an electrosurgical energy source.

3. An end effector assembly according to claim 1 wherein the potential of the at least one electrically conductive tissue sealing surface of the first jaw member and the potential of the cutting element are independently activatable by the surgeon.

4. An end effector assembly according to claim 1 wherein the electrical potential of the cutting element and the electrical potential of at least one electrically conductive tissue sealing surface are automatically configured for cutting when the surgeon selectively activates a trigger.

5. An end effector assembly according to claim 1 wherein the cutting element is substantially dull and only capable of cutting tissue through electrosurgical activation.

6. An end effector assembly according to claim 1 further comprising a smart sensor for determining seal quality prior to cutting.

7. An end effector assembly according to claim 6 wherein the smart sensor includes one of an audible or visual indicator for indicating seal quality.

8. An end effector assembly according to claim 6 wherein the smart sensor automatically switches electrosurgical energy to the cutting element once the tissue is sealed.

9. An end effector assembly according to claim 1 further comprising a first switch for energizing the electrically conductive tissue sealing surfaces to effect tissue sealing and a trigger for energizing the cutting element and at least one of the electrically conductive tissue sealing surfaces to effect tissue cutting.

10. An end effector assembly according to claim 1 wherein at least one of the insulators is configured to at least partially extend to a position which is at least substantially flush with the cutting element.

11. An end effector assembly according to claim 1 further comprising a second electrically conductive cutting element disposed within the insulator of the second jaw member, the second electrically conductive cutting element opposing the first electrically conductive cutting element.

12. An end effector assembly according to claim 11 wherein the first and second electrically conductive cutting elements when disposed on opposite sides of tissue form the gap distance between electrically conductive sealing surfaces when the jaw members are disposed in the second position.

13. An end effector assembly for use with an instrument for sealing and cutting vessels and/or tissue, the end effector assembly comprising:

a pair of opposing first and second jaw members at least one of which being movable relative to the other from a first position wherein the jaw members are disposed in spaced relation relative to one another to a second position wherein the jaw members cooperate to grasp tissue therebetween;

each jaw member including a pair of spaced apart, electrically conductive tissue sealing surfaces extending along a length thereof, each tissue sealing surface being adapted to connect to a source of electrosurgical energy such that the tissue sealing surfaces are capable of conducting electrosurgical energy through tissue held therebetween to effect a seal;

an insulator disposed between each pair of electrically conductive sealing surfaces;

the first jaw member including an electrically conductive cutting element disposed within the insulator of the first jaw member, the electrically conductive cutting element disposed in general vertical registration to the insulator on the second jaw member;

at least one stop member operatively associated with one of the first and second jaw members being dimensioned to create a gap between the electrically conductive tissue sealing surfaces when the jaw members close for sealing tissue;

the cutting element being inactive during the sealing process and the pair of spaced apart electrically conductive sealing surfaces on the first jaw member being energized to a different potential from the corresponding pair of spaced apart electrically conductive sealing surfaces on the second jaw member such that electrosurgical energy can be transferred through the tissue to effect a tissue seal; and the cutting element being energized to a first potential during the cutting process and at least one electrically conductive tissue sealing surface on the first jaw member and at least one electrically conductive tissue sealing surface on the second jaw member being energized to a different potential such that electrosurgical energy can be transferred through the tissue to effect a tissue cut.

* * * * *